United States Patent
Fauth et al.

(10) Patent No.: US 8,900,273 B2
(45) Date of Patent: Dec. 2, 2014

(54) TAPER-LOCKING FIXATION SYSTEM

(75) Inventors: Andrew R. Fauth, River Heights, UT (US); Daniel J. Triplett, Providence, UT (US); Joel R. Helgerson, Providence, UT (US)

(73) Assignee: GMEDelaware 2 LLC, Audubon, PA (US)

( * ) Notice: Subject to any disclaimer, the term of this patent is extended or adjusted under 35 U.S.C. 154(b) by 1374 days.

(21) Appl. No.: 11/972,158

(22) Filed: Jan. 10, 2008

(65) Prior Publication Data

US 2008/0167688 A1 Jul. 10, 2008

Related U.S. Application Data

(63) Continuation-in-part of application No. 11/063,941, filed on Feb. 22, 2005, now Pat. No. 7,993,373, and a (Continued)

(51) Int. Cl.
*A61B 17/58* (2006.01)
*A61B 17/56* (2006.01)
*A61B 17/70* (2006.01)

(52) U.S. Cl.
CPC ............ *A61B 17/704* (2013.01); *A61B 17/7035* (2013.01); *A61B 17/7041* (2013.01); *A61B 17/7011* (2013.01)
USPC ....................................................... 606/265

(58) Field of Classification Search
CPC .... A61B 17/56; A61B 17/58; A61B 17/7041; A61B 17/7035
USPC ........... 606/246–279, 280–299, 300–331, 60, 606/61
See application file for complete search history.

(56) References Cited

U.S. PATENT DOCUMENTS 2,677,369 A 5/1954 Knowles
3,247,000 A 4/1966 Taylor
(Continued)

FOREIGN PATENT DOCUMENTS

EP 408489 A1 1/1991
EP 322334 B1 2/1992
(Continued)

OTHER PUBLICATIONS

Goh JC, et al., "Influence of PLIF cage size on lumbar spine stability", Spine, Jan. 2000 25:1, PubMed abstract.
(Continued)

*Primary Examiner* — Christopher Beccia

(57) ABSTRACT

A fixation system is designed to lock an elongated member within a housing member, permitting positional and/or orientational adjustment of the elongated member prior to locking. The system includes a housing member, a slotted spherical collet, an elongated member, and may include a tapered wedge, which may be a discrete component or formed as part of the elongated member. The housing member and/or elongated member may be implantable. The elongated member may be positioned in the wedge, the wedge in the collet, and the collet in the housing such that when compression force is applied to the wedge and the collet, the wedge contracts about the elongated member and the collet expands to engage the housing, thus locking the elongated member relative to the housing. The collet may have a tapered channel with a degree of taper equal to the tapered wedge. The collet may have multiple slots to allow uniform radial expansion and compression.

22 Claims, 28 Drawing Sheets

Related U.S. Application Data continuation-in-part of application No. 11/312,323, filed on Dec. 19, 2005, now Pat. No. 8,062,336.

(60) Provisional application No. 60/884,233, filed on Jan. 10, 2007, provisional application No. 60/912,323, filed on Apr. 17, 2007, provisional application No. 60/968,324, filed on Aug. 28, 2007, provisional application No. 60/950,012, filed on Jul. 16, 2007, provisional application No. 60/950,021, filed on Jul. 16, 2007, provisional application No. 60/950,031, filed on Jul. 16, 2007, provisional application No. 60/950,038, filed on Jul. 16, 2007, provisional application No. 60/957,505, filed on Aug. 23, 2007, provisional application No. 60/968,925, filed on Aug. 30, 2007, provisional application No. 61/015,866, filed on Dec. 21, 2007, provisional application No. 61/015,876, filed on Dec. 21, 2007, provisional application No. 60/975,731, filed on Sep. 27, 2007, provisional application No. 60/984,798, filed on Nov. 2, 2007, provisional application No. 60/984,814, filed on Nov. 2, 2007, provisional application No. 60/984,983, filed on Nov. 2, 2007, provisional application No. 60/984,434, filed on Nov. 1, 2007, provisional application No. 60/984,428, filed on Nov. 1, 2007, provisional application No. 60/984,594, filed on Nov. 1, 2007, provisional application No. 61/014,344, filed on Dec. 17, 2007, provisional application No. 61/015,886, filed on Dec. 21, 2007, provisional application No. 61/015,840, filed on Dec. 21, 2007.

(56) References Cited

U.S. PATENT DOCUMENTS

| | | | |
|---|---|---|---|
| 3,298,372 | A | 1/1967 | Feingberg |
| 3,426,364 | A | 2/1969 | Lumb |
| 3,486,505 | A | 12/1969 | Morrison |
| 3,508,954 | A | 4/1970 | White et al. |
| 3,534,989 | A * | 10/1970 | Yonkers ................. 403/369 |
| 3,648,691 | A | 3/1972 | Lumb et al. |
| 3,857,642 | A | 12/1974 | Miller |
| 3,867,728 | A | 2/1975 | Stubstad et al. |
| 3,875,595 | A | 4/1975 | Froning |
| 4,003,376 | A | 1/1977 | McKay |
| 4,092,078 | A | 5/1978 | Klotz et al. |
| 4,289,123 | A | 9/1981 | Dunn |
| 4,349,921 | A | 9/1982 | Kuntz |
| 4,369,769 | A | 1/1983 | Edwards |
| 4,479,491 | A | 10/1984 | Martin |
| 4,483,334 | A | 11/1984 | Murray |
| 4,501,269 | A | 2/1985 | Bagby |
| 4,554,914 | A | 11/1985 | Kapp et al. |
| 4,599,086 | A | 7/1986 | Doty |
| 4,604,995 | A | 8/1986 | Stephens et al. |
| 4,611,581 | A | 9/1986 | Steffee |
| 4,641,636 | A | 2/1987 | Cotrel |
| 4,653,481 | A | 3/1987 | Howland et al. |
| 4,657,550 | A | 4/1987 | Daher |
| 4,696,290 | A | 9/1987 | Steffee |
| 4,743,260 | A | 5/1988 | Burton |
| 4,759,769 | A | 7/1988 | Hedman et al. |
| 4,772,287 | A | 9/1988 | Ray et al. |
| 4,790,303 | A | 12/1988 | Steffee |
| 4,800,874 | A | 1/1989 | David et al. |
| 4,805,602 | A | 2/1989 | Puno et al. |
| 4,827,918 | A | 5/1989 | Olerud |
| 4,863,476 | A | 9/1989 | Shepperd |
| 4,863,477 | A | 9/1989 | Monson |
| 4,892,545 | A | 1/1990 | Day et al. |
| 4,904,260 | A | 2/1990 | Ray et al. |
| 4,911,718 | A | 3/1990 | Lee et al. |
| 4,946,458 | A | 8/1990 | Harms et al. |
| 4,955,908 | A | 9/1990 | Frey et al. |
| 5,011,484 | A | 4/1991 | Breard |
| 5,015,255 | A | 5/1991 | Kuslich |
| 5,047,055 | A | 9/1991 | Bao et al. |
| 5,071,437 | A | 12/1991 | Steffee |
| 5,092,866 | A | 3/1992 | Breard et al. |
| 5,092,867 | A | 3/1992 | Harms et al. |
| 5,092,893 | A | 3/1992 | Smith |
| 5,127,912 | A | 7/1992 | Ray et al. |
| 5,129,900 | A | 7/1992 | Asher et al. |
| 5,147,361 | A | 9/1992 | Ojima et al. |
| 5,147,404 | A | 9/1992 | Downey |
| 5,171,279 | A | 12/1992 | Mathews |
| 5,171,280 | A | 12/1992 | Baumgartner |
| 5,180,393 | A | 1/1993 | Commarmond |
| 5,192,326 | A | 3/1993 | Bao et al. |
| 5,236,460 | A | 8/1993 | Barber |
| 5,246,458 | A | 9/1993 | Graham |
| 5,258,031 | A | 11/1993 | Salib et al. |
| 5,261,910 | A | 11/1993 | Warden et al. |
| 5,263,953 | A | 11/1993 | Bagby |
| 5,282,863 | A | 2/1994 | Burton |
| 5,304,178 | A | 4/1994 | Stahurski |
| 5,306,275 | A | 4/1994 | Bryan |
| 5,306,308 | A | 4/1994 | Gross et al. |
| 5,306,309 | A | 4/1994 | Wagner et al. |
| 5,313,962 | A | 5/1994 | Obenchain |
| 5,318,567 | A | 6/1994 | Vichard |
| 5,360,430 | A | 11/1994 | Lin |
| 5,366,455 | A | 11/1994 | Dove et al. |
| 5,370,697 | A | 12/1994 | Baumgartner |
| 5,375,823 | A | 12/1994 | Navas |
| 5,387,213 | A | 2/1995 | Breard et al. |
| 5,391,168 | A | 2/1995 | Sanders et al. |
| 5,401,269 | A | 3/1995 | Buttner-Janz et al. |
| 5,415,661 | A | 5/1995 | Holmes |
| 5,437,669 | A | 8/1995 | Yuan et al. |
| 5,437,672 | A | 8/1995 | Alleyne |
| 5,439,464 | A | 8/1995 | Shapiro |
| 5,443,516 | A | 8/1995 | Albrektsson et al. |
| 5,456,722 | A | 10/1995 | Mcleod et al. |
| 5,458,641 | A | 10/1995 | Ramirez Jimenez |
| 5,458,642 | A | 10/1995 | Beer et al. |
| 5,458,643 | A | 10/1995 | Oka et al. |
| 5,464,439 | A | 11/1995 | Gendler |
| 5,466,237 | A | 11/1995 | Byrd, III |
| 5,470,333 | A | 11/1995 | Ray |
| 5,476,463 | A | 12/1995 | Boachie-Adjei et al. |
| 5,480,401 | A | 1/1996 | Navas |
| 5,489,308 | A | 2/1996 | Kuslich et al. |
| 5,496,318 | A | 3/1996 | Howland et al. |
| 5,507,745 | A | 4/1996 | Logroscino et al. |
| 5,507,813 | A | 4/1996 | Dowd et al. |
| 5,514,180 | A | 5/1996 | Heggeness et al. |
| 5,522,899 | A | 6/1996 | Michelson |
| 5,527,312 | A | 6/1996 | Ray |
| 5,531,745 | A | 7/1996 | Ray |
| 5,531,747 | A | 7/1996 | Ray |
| 5,534,028 | A | 7/1996 | Bao et al. |
| 5,534,030 | A | 7/1996 | Navarro et al. |
| 5,534,031 | A | 7/1996 | Matsuzaki et al. |
| 5,540,688 | A | 7/1996 | Navas |
| 5,545,166 | A | 8/1996 | Howland |
| 5,545,229 | A | 8/1996 | Parsons et al. |
| 5,549,607 | A | 8/1996 | Olson et al. |
| 5,556,431 | A | 9/1996 | Buttner-Janz |
| 5,556,687 | A | 9/1996 | McMillin |
| 5,562,735 | A | 10/1996 | Margulies |
| 5,562,736 | A | 10/1996 | Ray et al. |
| 5,562,737 | A | 10/1996 | Graf |
| 5,569,248 | A | 10/1996 | Mathews |
| 5,571,189 | A | 11/1996 | Kuslich |
| 5,571,191 | A | 11/1996 | Fitz |
| 5,572,191 | A | 11/1996 | Lundberg |
| 5,582,612 | A | 12/1996 | Lin |
| 5,584,832 | A | 12/1996 | Schlapfer |
| 5,603,713 | A | 2/1997 | Aust et al. |
| 5,609,634 | A | 3/1997 | Voydeville |

(56) References Cited

U.S. PATENT DOCUMENTS

| | | |
|---|---|---|
| 5,645,597 A | 7/1997 | Krapiva |
| 5,645,599 A | 7/1997 | Samani |
| 5,649,926 A | 7/1997 | Howland |
| 5,653,762 A | 8/1997 | Pisharodi |
| 5,666,243 A | 9/1997 | Brent |
| 5,672,175 A | 9/1997 | Martin |
| 5,674,295 A | 10/1997 | Ray et al. |
| 5,674,296 A | 10/1997 | Bryan |
| 5,676,701 A | 10/1997 | Yuan et al. |
| 5,681,310 A | 10/1997 | Yuan et al. |
| 5,683,464 A | 11/1997 | Wagner et al. |
| 5,683,465 A | 11/1997 | Shinn et al. |
| 5,688,272 A | 11/1997 | Montague et al. |
| 5,690,629 A | 11/1997 | Asher et al. |
| 5,702,392 A | 12/1997 | Wu et al. |
| 5,702,450 A | 12/1997 | Bisserie |
| 5,702,453 A | 12/1997 | Rabbe et al. |
| 5,704,936 A | 1/1998 | Mazel |
| 5,713,900 A | 2/1998 | Benzel et al. |
| 5,716,415 A | 2/1998 | Steffee |
| 5,725,582 A | 3/1998 | Bevan et al. |
| 5,728,097 A | 3/1998 | Mathews |
| 5,735,899 A | 4/1998 | Schwartz et al. |
| 5,749,873 A | 5/1998 | Fairley |
| 5,755,796 A | 5/1998 | Ibo et al. |
| 5,772,661 A | 6/1998 | Michelson |
| 5,797,909 A | 8/1998 | Michelson |
| 5,814,046 A | 9/1998 | Hopf |
| 5,824,093 A | 10/1998 | Ray et al. |
| 5,824,094 A | 10/1998 | Serhan et al. |
| 5,836,948 A | 11/1998 | Zucherman et al. |
| 5,860,977 A | 1/1999 | Zucherman et al. |
| 5,865,846 A | 2/1999 | Bryan et al. |
| 5,868,745 A | 2/1999 | Alleyne |
| 5,876,404 A | 3/1999 | Zucherman et al. |
| 5,888,223 A | 3/1999 | Bray, Jr. |
| 5,893,889 A | 4/1999 | Harrington |
| RE36,221 E | 6/1999 | Breard et al. |
| 5,910,142 A * | 6/1999 | Tatar ............................ 606/272 |
| 5,916,267 A | 6/1999 | Tienboon |
| 5,951,555 A | 9/1999 | Rehak et al. |
| 5,961,516 A | 10/1999 | Graf |
| 5,986,169 A | 11/1999 | Gjunter |
| 6,001,130 A | 12/1999 | Bryan et al. |
| 6,004,322 A | 12/1999 | Bernstein |
| 6,014,588 A | 1/2000 | Fitz |
| 6,019,759 A | 2/2000 | Rogozinski |
| 6,019,792 A | 2/2000 | Cauthen |
| 6,039,761 A | 3/2000 | Li et al. |
| 6,039,763 A | 3/2000 | Shelokov |
| 6,048,342 A | 4/2000 | Zucherman et al. |
| 6,053,917 A * | 4/2000 | Sherman et al. .............. 606/270 |
| 6,063,088 A | 5/2000 | Winslow |
| 6,063,121 A | 5/2000 | Xavier et al. |
| 6,066,325 A | 5/2000 | Wallace et al. |
| 6,068,630 A | 5/2000 | Zucherman et al. |
| RE36,758 E | 6/2000 | Fitz |
| 6,074,390 A | 6/2000 | Zucherman et al. |
| 6,080,157 A | 6/2000 | Cathro et al. |
| 6,090,112 A | 7/2000 | Zucherman et al. |
| 6,093,205 A | 7/2000 | McLeod et al. |
| 6,113,637 A | 9/2000 | Gill et al. |
| 6,113,639 A | 9/2000 | Ray et al. |
| 6,132,464 A | 10/2000 | Martin |
| 6,132,465 A | 10/2000 | Ray et al. |
| 6,146,421 A | 11/2000 | Gordon et al. |
| 6,149,652 A | 11/2000 | Zucherman et al. |
| 6,151,934 A | 11/2000 | Chong et al. |
| 6,152,926 A | 11/2000 | Zucherman et al. |
| 6,156,038 A | 12/2000 | Zucherman et al. |
| 6,156,067 A | 12/2000 | Bryan et al. |
| 6,176,861 B1 | 1/2001 | Bernstein et al. |
| 6,179,838 B1 | 1/2001 | Fiz |
| 6,183,471 B1 | 2/2001 | Zucherman et al. |
| 6,187,005 B1 * | 2/2001 | Brace et al. .................. 606/264 |
| 6,189,422 B1 | 2/2001 | Stihl |
| 6,190,387 B1 | 2/2001 | Zucherman et al. |
| 6,190,414 B1 | 2/2001 | Young et al. |
| 6,206,882 B1 | 3/2001 | Cohen |
| 6,206,922 B1 | 3/2001 | Zdeblick et al. |
| 6,228,118 B1 | 5/2001 | Gordon |
| 6,235,030 B1 | 5/2001 | Zucherman et al. |
| 6,238,397 B1 | 5/2001 | Zucherman et al. |
| 6,241,730 B1 | 6/2001 | Alby |
| 6,264,655 B1 | 7/2001 | Pisharodi |
| 6,267,764 B1 | 7/2001 | Elberg |
| 6,280,444 B1 | 8/2001 | Zucherman et al. |
| 6,290,700 B1 | 9/2001 | Schmotzer |
| 6,293,949 B1 | 9/2001 | Justis et al. |
| 6,312,469 B1 | 11/2001 | Gielen et al. |
| 6,314,325 B1 | 11/2001 | Fitz |
| 6,332,882 B1 | 12/2001 | Zucherman et al. |
| 6,332,883 B1 | 12/2001 | Zucherman et al. |
| 6,379,355 B1 | 4/2002 | Zucherman et al. |
| 6,402,750 B1 | 6/2002 | Atkinson et al. |
| 6,413,259 B1 | 7/2002 | Lyons et al. |
| 6,419,676 B1 | 7/2002 | Zucherman et al. |
| 6,419,677 B2 | 7/2002 | Zucherman et al. |
| 6,419,703 B1 | 7/2002 | Fallin et al. |
| 6,419,704 B1 | 7/2002 | Ferree |
| 6,440,169 B1 | 8/2002 | Elberg et al. |
| 6,447,546 B1 | 9/2002 | Bramlet et al. |
| 6,451,019 B1 | 9/2002 | Zucherman et al. |
| 6,451,020 B1 | 9/2002 | Zucherman et al. |
| 6,458,131 B1 | 10/2002 | Ray |
| 6,461,359 B1 | 10/2002 | Tribus et al. |
| 6,471,704 B2 | 10/2002 | Gertzbein et al. |
| 6,475,219 B1 | 11/2002 | Shelokov |
| 6,478,796 B2 | 11/2002 | Zucherman et al. |
| 6,481,440 B2 | 11/2002 | Gielen et al. |
| 6,485,518 B1 | 11/2002 | Cornwall et al. |
| 6,500,178 B2 | 12/2002 | Zucherman et al. |
| 6,514,256 B2 | 2/2003 | Zucherman et al. |
| 6,527,806 B2 | 3/2003 | Ralph et al. |
| 6,540,747 B1 | 4/2003 | Marino |
| 6,540,785 B1 | 4/2003 | Gill et al. |
| 6,565,605 B2 | 5/2003 | Goble et al. |
| 6,579,319 B2 | 6/2003 | Goble et al. |
| 6,582,433 B2 | 6/2003 | Yun |
| 6,585,769 B1 | 7/2003 | Muhanna et al. |
| 6,610,091 B1 | 8/2003 | Reiley |
| 6,616,669 B2 | 9/2003 | Ogilvie et al. |
| 6,626,909 B2 | 9/2003 | Chin |
| 6,626,944 B1 | 9/2003 | Taylor |
| 6,652,527 B2 | 11/2003 | Zucherman et al. |
| 6,652,534 B2 | 11/2003 | Zucherman et al. |
| 6,652,585 B2 | 11/2003 | Lange |
| 6,660,005 B2 | 12/2003 | Toyama |
| 6,669,729 B2 | 12/2003 | Chin |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,733,534 B2 | 5/2004 | Sherman |
| 6,761,719 B2 | 7/2004 | Justis et al. |
| 6,761,720 B1 | 7/2004 | Senegas |
| 6,783,527 B2 | 8/2004 | Drewry et al. |
| 6,796,983 B1 | 9/2004 | Zucherman et al. |
| 6,811,567 B2 * | 11/2004 | Reiley ........................ 623/17.11 |
| 6,835,205 B2 | 12/2004 | Atkinson et al. |
| 6,835,207 B2 | 12/2004 | Zacouto et al. |
| 7,087,084 B2 | 8/2006 | Reiley |
| 7,261,714 B2 * | 8/2007 | Richelsoph ..................... 606/60 |
| 7,678,112 B2 * | 3/2010 | Rezach ........................... 606/60 |
| 2001/0007073 A1 | 7/2001 | Zucherman et al. |
| 2001/0012938 A1 | 8/2001 | Zucherman et al. |
| 2001/0016743 A1 | 8/2001 | Zucherman et al. |
| 2001/0021850 A1 | 9/2001 | Zucherman et al. |
| 2001/0031965 A1 | 10/2001 | Zucherman et al. |
| 2001/0039452 A1 | 11/2001 | Zucherman et al. |
| 2002/0029039 A1 | 3/2002 | Zucherman et al. |
| 2002/0065557 A1 | 5/2002 | Goble et al. |
| 2002/0072800 A1 | 6/2002 | Goble et al. |
| 2002/0091446 A1 | 7/2002 | Zucherman et al. |
| 2002/0099384 A1 | 7/2002 | Scribner et al. |

(56) References Cited

U.S. PATENT DOCUMENTS

| | | |
|---|---|---|
| 2002/0116000 A1 | 8/2002 | Zucherman et al. |
| 2002/0123806 A1 | 9/2002 | Reiley |
| 2002/0143331 A1 | 10/2002 | Zucherman et al. |
| 2002/0151895 A1 | 10/2002 | Soboleski et al. |
| 2002/0183746 A1 | 12/2002 | Zucherman et al. |
| 2003/0004572 A1 | 1/2003 | Goble et al. |
| 2003/0009226 A1 | 1/2003 | Graf |
| 2003/0028250 A1 | 2/2003 | Reiley et al. |
| 2003/0040797 A1 | 2/2003 | Fallin et al. |
| 2003/0055427 A1 | 3/2003 | Graf |
| 2003/0065330 A1 | 4/2003 | Zucherman et al. |
| 2003/0073998 A1 | 4/2003 | Pagliuca et al. |
| 2003/0109880 A1 | 6/2003 | Shirado et al. |
| 2003/0153912 A1 | 8/2003 | Graf |
| 2003/0191470 A1 | 10/2003 | Ritland |
| 2003/0212398 A1* | 11/2003 | Jackson ................ 606/61 |
| 2003/0220642 A1 | 11/2003 | Freudiger |
| 2003/0220643 A1 | 11/2003 | Ferree |
| 2004/0006341 A1 | 1/2004 | Shaolian et al. |
| 2004/0006391 A1 | 1/2004 | Reiley |
| 2004/0024458 A1 | 2/2004 | Senegas et al. |
| 2004/0049189 A1 | 3/2004 | Le Couedic et al. |
| 2004/0049190 A1 | 3/2004 | Biedermann et al. |
| 2004/0049272 A1 | 3/2004 | Reiley |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049281 A1 | 3/2004 | Reiley |
| 2004/0073215 A1 | 4/2004 | Carli |
| 2004/0078082 A1 | 4/2004 | Lange |
| 2004/0082954 A1 | 4/2004 | Teitelbaum et al. |
| 2004/0087950 A1 | 5/2004 | Teitelbaum |
| 2004/0106995 A1 | 6/2004 | Le Couedic et al. |
| 2004/0111154 A1 | 6/2004 | Reiley |
| 2004/0116927 A1 | 6/2004 | Graf |
| 2004/0117017 A1 | 6/2004 | Pasquet et al. |
| 2004/0127989 A1 | 7/2004 | Dooris et al. |
| 2004/0143264 A1 | 7/2004 | Mcafee |
| 2004/0147928 A1 | 7/2004 | Landry et al. |
| 2004/0153071 A1 | 8/2004 | Zucherman et al. |
| 2004/0158245 A1 | 8/2004 | Chin |
| 2004/0167520 A1 | 8/2004 | Zucherman et al. |
| 2004/0172025 A1 | 9/2004 | Drewry et al. |
| 2004/0181282 A1 | 9/2004 | Zucherman et al. |
| 2004/0181285 A1 | 9/2004 | Simonson |
| 2004/0186475 A1 | 9/2004 | Falahee |
| 2004/0220568 A1 | 11/2004 | Zucherman et al. |
| 2004/0225289 A1 | 11/2004 | Biedermann et al. |
| 2004/0230192 A1 | 11/2004 | Graf |
| 2004/0230201 A1 | 11/2004 | Yuan et al. |
| 2004/0230304 A1 | 11/2004 | Yuan et al. |
| 2004/0236327 A1 | 11/2004 | Paul et al. |
| 2004/0236328 A1 | 11/2004 | Paul et al. |
| 2004/0236329 A1 | 11/2004 | Panjabi |
| 2004/0243239 A1 | 12/2004 | Taylor |
| 2005/0010291 A1 | 1/2005 | Stinson et al. |
| 2005/0010293 A1 | 1/2005 | Zucherman et al. |
| 2005/0010298 A1 | 1/2005 | Zucherman et al. |
| 2005/0027361 A1 | 2/2005 | Reiley |
| 2005/0043797 A1 | 2/2005 | Lee |
| 2005/0043799 A1 | 2/2005 | Reiley |
| 2005/0055096 A1 | 3/2005 | Serham et al. |
| 2005/0070899 A1* | 3/2005 | Doubler et al. ............ 606/61 |
| 2005/0119748 A1* | 6/2005 | Reiley et al. ............ 623/17.11 |
| 2005/0131406 A1 | 6/2005 | Reiley et al. |
| 2005/0137705 A1 | 6/2005 | Reiley |
| 2005/0137706 A1 | 6/2005 | Reiley |
| 2005/0143818 A1* | 6/2005 | Yuan et al. ............ 623/17.11 |
| 2005/0149190 A1 | 7/2005 | Reiley |
| 2005/0154467 A1 | 7/2005 | Peterman et al. |
| 2005/0177166 A1 | 8/2005 | Timm |
| 2005/0228400 A1 | 10/2005 | Chao et al. |
| 2005/0240265 A1 | 10/2005 | Kuiper et al. |
| 2006/0052785 A1 | 3/2006 | Augostino et al. |
| 2006/0079903 A1 | 4/2006 | Wong |
| 2006/0195104 A1* | 8/2006 | Schlafli et al. ................ 606/72 |
| 2006/0217718 A1* | 9/2006 | Chervitz et al. ............... 606/61 |
| 2006/0282074 A1 | 12/2006 | Renaud et al. |
| 2007/0123860 A1* | 5/2007 | Francis et al. ................ 606/61 |
| 2008/0021454 A1* | 1/2008 | Chao et al. ..................... 606/61 |
| 2008/0200918 A1 | 8/2008 | Spitler et al. |
| 2008/0282846 A1 | 11/2008 | Sharifi-Mehr et al. |
| 2009/0163963 A1 | 6/2009 | Berrevoets |

FOREIGN PATENT DOCUMENTS

| | | |
|---|---|---|
| EP | 667127 A1 | 8/1995 |
| EP | 767637 B1 | 11/1998 |
| EP | 768843 B1 | 2/1999 |
| EP | 669109 B1 | 5/1999 |
| EP | 1239785 B1 | 9/2004 |
| EP | 1343424 B1 | 9/2004 |
| EP | 1399078 B1 | 12/2004 |
| FR | 2721501 B1 | 8/1996 |
| JP | 10179622 A2 | 7/1998 |
| JP | 10277070 A2 | 10/1998 |
| SU | 1468543 A1 | 3/1989 |
| SU | 1517953 A1 | 10/1989 |
| WO | WO8707827 A1 | 12/1987 |
| WO | WO9421185 A1 | 9/1994 |
| WO | WO9505783 A1 | 3/1995 |
| WO | WO9505784 A1 | 3/1995 |
| WO | WO9505785 A1 | 3/1995 |
| WO | WO9505786 A1 | 3/1995 |
| WO | WO9600049 A1 | 1/1996 |
| WO | WO9822033 A1 | 5/1998 |
| WO | WO9848707 A1 | 11/1998 |
| WO | WO9848717 A1 | 11/1998 |
| WO | WO9856301 A1 | 12/1998 |
| WO | WO9905995 A1 | 2/1999 |
| WO | WO9921500 A1 | 5/1999 |
| WO | WO9921501 A1 | 5/1999 |
| WO | WO9923963 A1 | 5/1999 |
| WO | WO9965412 A1 | 12/1999 |
| WO | WO9960957 A1 | 5/2000 |
| WO | WO0038582 | 7/2000 |
| WO | WO0062684 A1 | 10/2000 |
| WO | WO0130248 A1 | 5/2001 |
| WO | WO0145576 A1 | 6/2001 |
| WO | WO0149192 A1 | 7/2001 |
| WO | WO0156489 A1 | 8/2001 |
| WO | WO0164142 A1 | 9/2001 |
| WO | WO0164144 A2 | 9/2001 |
| WO | WO0191657 A1 | 12/2001 |
| WO | WO0191658 A1 | 12/2001 |
| WO | WO0197721 A2 | 12/2001 |
| WO | WO0200124 A1 | 1/2002 |
| WO | WO0203882 A2 | 1/2002 |
| WO | WO0207621 A1 | 1/2002 |
| WO | WO0207622 A1 | 1/2002 |
| WO | WO0207623 A1 | 1/2002 |
| WO | WO0230336 A2 | 4/2002 |
| WO | WO0234120 A2 | 5/2002 |
| WO | WO0243603 A1 | 6/2002 |
| WO | WO02067792 A2 | 9/2002 |
| WO | WO02067793 A2 | 9/2002 |
| WO | WO02089712 A1 | 11/2002 |
| WO | WO02102259 A2 | 12/2002 |
| WO | WO03009737 A1 | 2/2003 |
| WO | WO03011147 A1 | 2/2003 |
| WO | WO03015646 A2 | 2/2003 |
| WO | WO03045262 A2 | 6/2003 |
| WO | WO03077806 A1 | 9/2003 |
| WO | WO2004017817 A2 | 3/2004 |
| WO | WO2004019762 A2 | 3/2004 |
| WO | WO2004024010 A1 | 3/2004 |
| WO | WO2004032794 A2 | 4/2004 |
| WO | WO2004039239 A2 | 5/2004 |
| WO | WO2004039243 A2 | 5/2004 |
| WO | WO2004041066 A2 | 5/2004 |
| WO | WO2004073533 A1 | 9/2004 |

(56) References Cited

FOREIGN PATENT DOCUMENTS

| WO | WO2004098423 A1 | 11/2004 |
|---|---|---|
| WO | WO2004098452 A2 | 11/2004 |
| WO | WO2004105577 A2 | 12/2004 |
| WO | WO2004105580 A2 | 12/2004 |
| WO | WO2005013864 | 2/2005 |
| WO | WO2005037149 | 4/2005 |
| WO | WO2005044152 A1 | 5/2005 |

OTHER PUBLICATIONS

Head WC, Wagner surface replacement arthroplasty of the hip. Analysis of fourteen failures in forty-one hips:, J Bone Joint Surg. [Am], Mar. 1981 63:3, PubMed Abstract.

Kotani Y, et al., "The effects of spinal fixation and destabilization on the biomechanical and histologic properties of spinal ligaments. An in vivo study.", Spine, Mar. 15, 1998 23:6, PubMed abstract.

Lemaire JP, et al., "Intervertebral Disc Prosthesis: Results and Prospects for the Year 2000", Clinical Orthopaedics and Related Research, PubMed abstract.

Nagata H, et al., "The effects of immobilization of long segments of the spine on the adjacent and distal facet force and lumbrosacral motion", Spine, Dec. 1993 18:16. PubMed abstract.

Nibu K, et al., Multidirectional stabilizing potential of BAK interbody spinal fusion system for anterior surgery, J Spinal Discord, Aug. 1997 10:4, PubMed abstract.

Tsantrizos A, et al., "Segmental stability and compressive strength of posterior lumbar interbody fusion implants", Spine, Aug. 1, 2000 25:15, PubMed abstract.

Todd Anres; *Facet Joint Arthroplasty: A Glimpse of the Future of Spine Technology*, Othopaedic Product News, Sep./Oct. 2005 p. 38,40.

IPRP and Written Opinion in matter PCT/US2009/066761.

ISR in matter PCT/US2009/066761.

\* cited by examiner

TAPER-LOCKING FIXATION SYSTEM

CROSS-REFERENCE TO RELATED APPLICATIONS

This application is a continuation-in-part of the following, which are incorporated herein by reference:

pending U.S. application Ser. No. 11/063,941, filed Feb. 22, 2005, which is entitled POLYAXIAL ORTHOPEDIC FASTENING APPARATUS; and pending U.S. application Ser. No. 11/312,323, filed Dec. 19, 2005, which is entitled POLYAXIAL ORTHOPEDIC FASTENING APPARATUS WITH INDEPENDENT LOCKING MODES.

This application claims the benefit of the following, which is are incorporated herein by reference:

U.S. Provisional Patent Application No. 60/884,233, filed Jan. 10, 2007, which is entitled TAPER-LOCKING ROD FIXATION SYSTEM;

U.S. Provisional Patent Application No. 60/912,323, filed Apr. 17, 2007, which is entitled AFRS MULTI-LEVEL IMPLANT SYSTEM;

U.S. Provisional Patent Application No. 60/968,324, filed Aug. 27, 2007, which is entitled INTERVERTEBRAL DISC IMPLANT WITH FACET MOTION CONSTRAINTS;

U.S. Provisional Patent Application No. 60/950,012, filed Jul. 16, 2007, which is entitled INFERIOR FACET IMPLANT HOLDER WITH CLAMP RETENTION;

U.S. Provisional Patent Application No. 60/950,021, filed Jul. 16, 2007, which is entitled MONORAIL INSTRUMENT GUIDANCE SYSTEM FOR LUMBAR SPINAL SURGERY;

U.S. Provisional Patent Application No. 60/950,031, filed Jul. 16, 2007, which is entitled LINEAR POLYAXIAL LOCKING MECHANISM WITH TOOL;

U.S. Provisional Patent Application No. 60/950,038, filed Jul. 16, 2007, which is entitled MOBILE INFERIOR FACET BEARING WITH SUPERIOR CLIP;

U.S. Provisional Patent Application No. 60/957,505, filed Aug. 23, 2007, which is entitled DYNAMIC STABILIZATION AND STATIC FIXATION OPTIONS FOR FACET REPLACEMENT PROSTHESIS;

U.S. Provisional Patent Application No. 60/968,925, filed Aug. 30, 2007, which is entitled SYSTEMS AND METHODS FOR LESS INVASIVE FACET JOINT REPLACEMENT;

U.S. Provisional Patent Application No. 61/015,866, filed Dec. 21, 2007, which is entitled INTERVERTEBRAL DISC IMPLANT WITH FACET MOTION CONSTRAINTES INCLUDING POSTERIOR COMBINATION DISCS;

U.S. Provisional Patent Application No. 61/015,876, filed Dec. 21, 2007, which is entitled INTERVERTEBRAL DISC IMPLANT WITH FACET MOTION CONSTRAINTS AND METHODS FOR IMPLANT ALIGNMENT;

U.S. Provisional Patent Application No. 60/975,731, filed Sep. 28, 2007, which is entitled MONOLITHIC INFERIOR IMPLANT STRUT WITH INTEGRAL CROSS LINK CLAMP;

U.S. Provisional Patent Application No. 60/984,798, filed Nov. 2, 2007, which is entitled LOW PROFILE POLYAXIAL FACET IMPLANT;

U.S. Provisional Patent Application No. 60/984,814, filed Nov. 2, 2007, which is entitled HINGED EYELET SCREW;

U.S. Provisional Patent Application No. 60/984,983, filed Nov. 2, 2007, which is entitled ADJUSTABLE FACET IMPLANT BASE PIECE;

U.S. Provisional Patent Application No. 60/984,434, filed Nov. 1, 2007, which is entitled SUPERIOR INSTRUMENTS;

U.S. Provisional Patent Application No. 60/984,428, filed Nov. 1, 2007, which is entitled CROSS LINK CLAMP;

U.S. Provisional Patent Application No. 60/984,594, filed Nov. 1, 2007, which is entitled ADJUSTABLE INFERIOR FACET REPLACEMENT WITH MEDIAL-LATER SLIDE ADJUSTMENT;

U.S. Provisional Patent Application No. 61/014,344, filed Dec. 17, 2007, which is entitled INFERIOR STRUT UPDATE;

U.S. Provisional Patent Application No. 61/015,886, filed Dec. 21, 2007, which is entitled EYELET PEDICLE SCREW TIH MULTI-AXIAL FIXATION; and U.S. Provisional Patent Application No. 61/015,840, filed Dec. 21, 2007, which is entitled CERVICAL PLATE WITH FACET MOTION CONTROL.

BACKGROUND OF THE INVENTION

1. The Field of the Invention

The invention relates mechanical methods for securing an off-axis member within a second member. The present invention generally describes a mechanism by which a rod or rod-like device is secured within a second member via a taper-lock.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION

The present invention advances the state of the art by providing systems and methods that can be used to anchor orthopedic implants to bone in a manner that provides a high degree of implant adjustability, simplicity, and ease of use. The self-locking taper mechanism herein described is designed to secure a cylindrical rod within a receiving member or other device. In the case of spinal fixation, this taper lock would secure fixation between two or more vertebrae. The primary embodiment of the present invention concerns securing a spinal fixation rod to a fixation member such as a pedicle screw or intermediate attachment to the pedicle. The present invention can be used in any orthopedic procedure, but may have particular utility in the field of facet joint replacement to alleviate back pain resulting from traumatic, inflammatory, metabolic, synovial, neoplastic and degenerative spinal disorders. However, it is understood within the scope of the invention that elements of the implant beyond the rod fixation member can vary to be used for spinal fixation, facet arthroplasty, multi-level facet arthroplasty, combination of facet arthroplasty and spinal fixation, cross-linking between spinal implants, or other applications.

In this application, "polyaxial" rotation is rotation that can occur about at least two axes that are not parallel to each other. "Lock-out" between two or more component parts refers to a state in which movement of any component part is prevented by frictional, compression, expansion, or other forces. A "taper-lock connector" refers to any locking mechanism that uses a taper to effect locking. "Uniform radial expansion" refers to radial expansion in which the radius increases substantially the same distance at each location on the circumference, that is, one portion does not increase significantly more or less.

Figure 1:
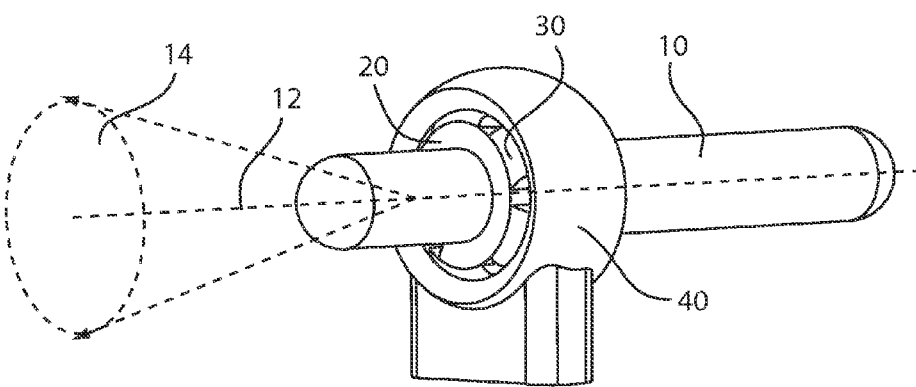
FIG. 1 is a perspective view of a rod fixation system consisting of an implant member, a spherical collet, a tapered wedge, and a cylindrical rod.

FIG. 1 illustrates the main components needed for the preferred embodiment of the taper-lock fixation system herein described. The self-locking taper mechanism is shown to secure a cylindrical rod 10 within an implant member 40. Rod 10 is passed through tapered wedge 20, which in turn sits within spherical collet 30. The entire assembly of rod 10, wedge 20 and collet 30 is contained within implant member 40, which has a spherical inner surface, allowing the rod-taper lock assembly to have polyaxial motion prior to lock-out. The cone 14 of polyaxial motion which is allowed prior to lock-out is shown in FIG. 1 along the axis 12 through the opening of the implant member 40. Rod 10 is designed to initially pass through wedge 20 freely allowing the position of rod 10 relative to the wedge 20 and collet 30 to be completely adjustable prior to lock-out. Additionally, the orientation of rod 10 can be adjusted in a polyaxial or conical manner due to the spherical articulation between collet 30 and implant 40. Once the desired position and orientation of rod 10 is determined, the system is locked out.

Figure 2:
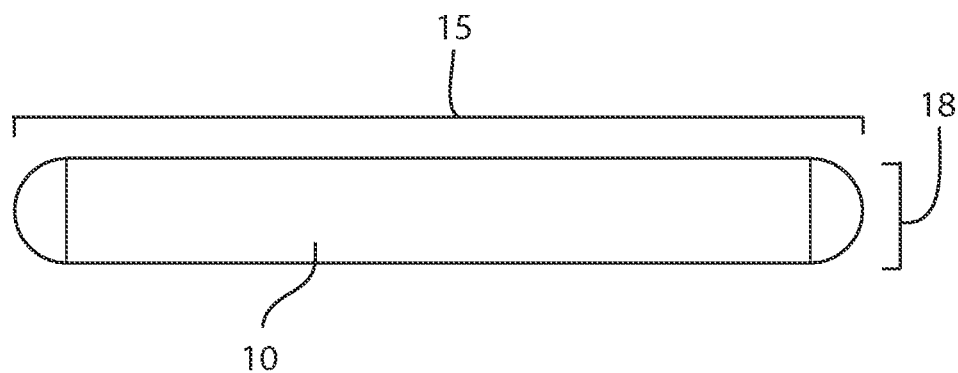
FIG. 2 shows an example of a cylindrical rod.

The cylindrical rod 10 is illustrated further in FIG. 2. In the present embodiment, cylindrical rod 10 may encompass any elongated member of varying length 15 and diameter 18. However, it can be appreciated by one skilled in the art that elongated members of other lengths, diameters and configurations may be used. The elongated member may be entirely straight, curved along a segment, bent, tapered, or otherwise configured. In addition, the elongated member may be a discrete element as depicted in FIG. 2, or may be joined to or monolithically formed with other components.

Figure 3:
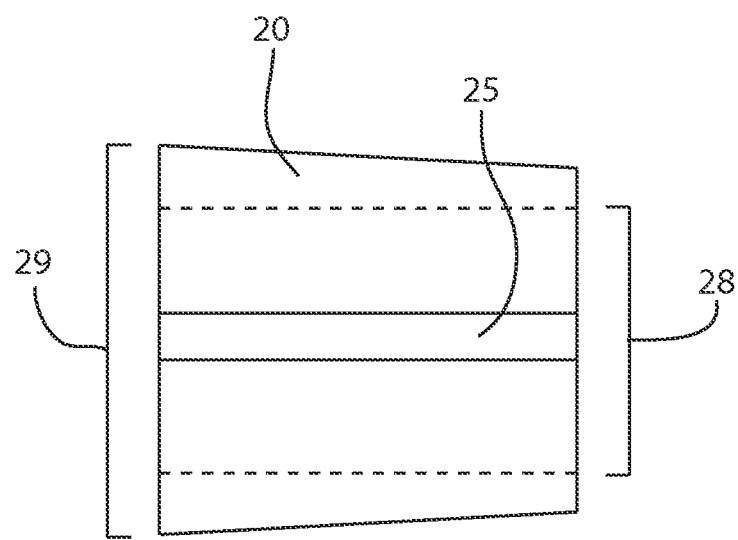
FIG. 3 is a side view of a tapered wedge.
Figure 4:
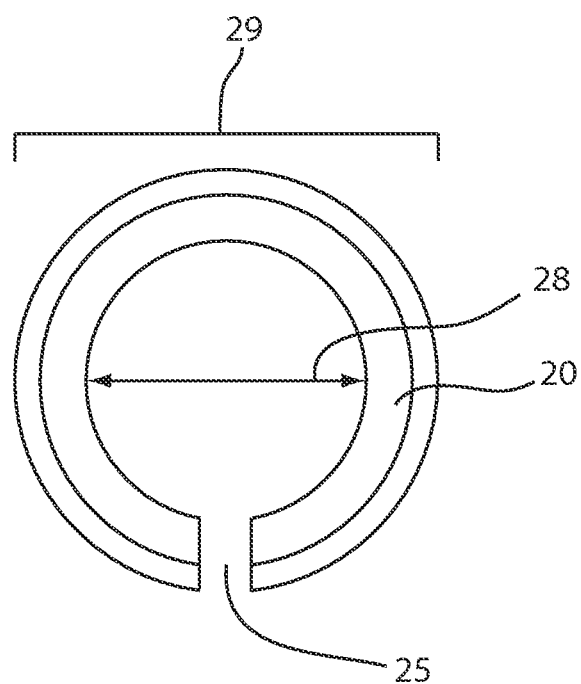
FIG. 4 is a top view of the tapered wedge of FIG. 3.

Wedge 20 is illustrated further in FIGS. 3 and 4. In the present invention, tapered wedge 20 describes any wedge piece comprised of cylindrical inner diameter 28 and tapered outer diameter 29. Inner diameter 28 is configured to receive cylindrical rod 10. The tapered wedge 20 shown in FIGS. 3 and 4 also contains at least one opening or slot 25 down one side, to allow for contraction of wedge 20. It is understood within the scope of the present invention that wedge 20 may have varying degrees of taper and/or varying lengths. It is also understood that the length, width, number of and/or orientation of slots 25 can be varied.

Figure 5:
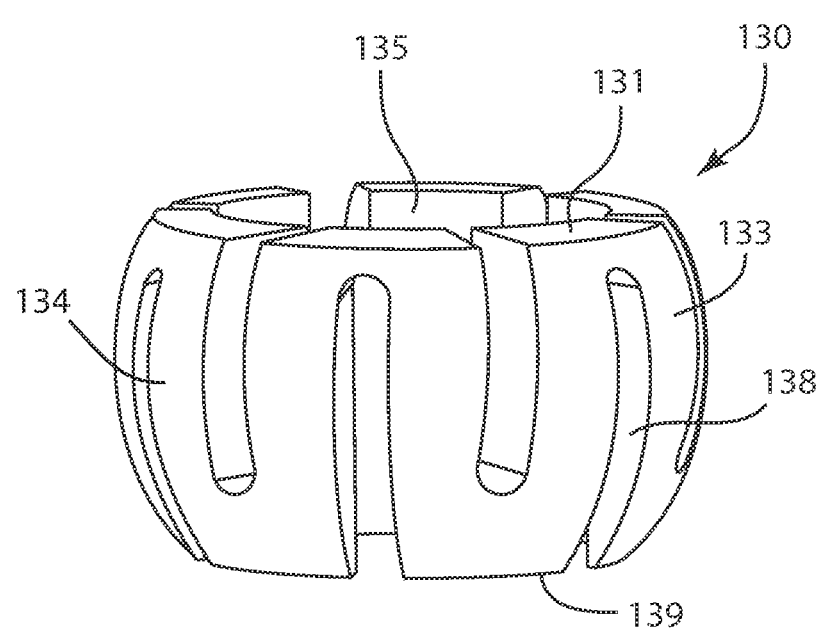
FIG. 5 is a perspective view of one embodiment of a spherical collet.

The spherical collet 30 shown in FIG. 1 and described above may include various embodiments. FIG. 5 shows one embodiment of a spherical collet. Spherical collet 130 of FIG. 5 consists of a spherical body 133, which has flat top 131 and bottom 139. A hollow, conical channel 135 runs through the center of collet 130 for receiving tapered wedge 20. Channel 135 may taper from top 131 to bottom 139, and the degree of the taper may be the same as the taper of the wedge piece 20. An outer convex wall 134 of collet 130 may be roughened to provide friction when locked-out, and the outer convex wall 134 includes a plurality of slots 138 to allow the sphere to expand and contract. The multiple slots 138 create between them multiple outer surface sections on the collet, allowing for more points of contact with the inner surface of the implant 40 when the taper-lock is assembled. The multiple slots additionally allow substantially uniform radial expansion and compression of the collet, since each section of the collet between the slots can expand or contract the same distance.

Figure 6:
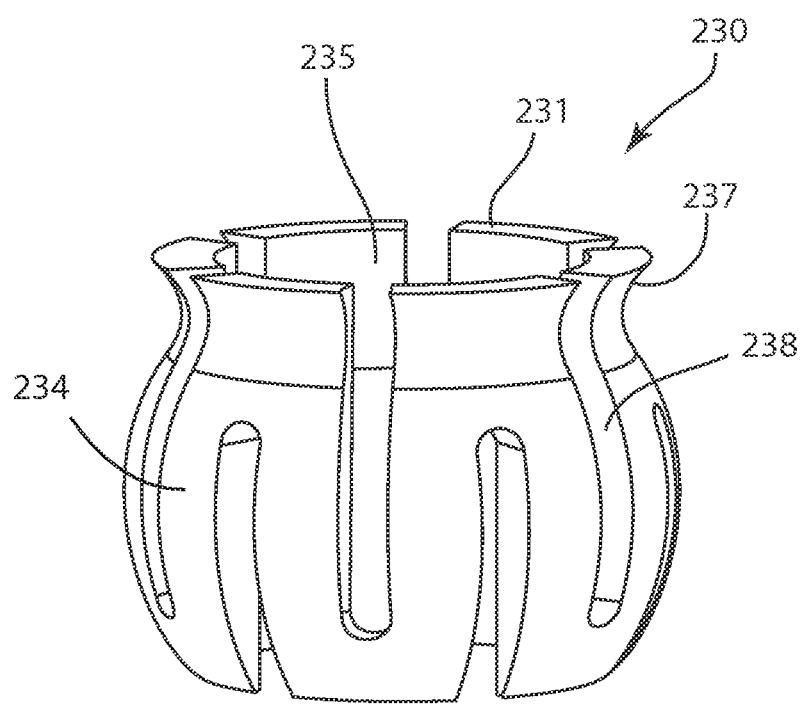
FIG. 6 is a perspective view of another embodiment of a spherical collet.

In alternative embodiments of spherical collet 30, the top surface of the sphere may be varied in its geometry. One such embodiment is shown in FIG. 6. Collet 230 of FIG. 6 is similar to collet 130 of FIG. 5. Collet 230 includes channel 235 through its center as well as slots 238 along an outer convex wall 234 to allow for expansion and contraction. However, collet 230 includes flange 237 on the top surface 231 of the collet. Flange 237 may be helpful in creating a surface for the application of force by instrumentation. Other embodiments may include a flange which is not curved but straight, or a rim which projects longitudinally from the top of the sphere but does not extend outward. A flange or rim portion on the collet may limit over-rotation or other undesired movement of the sphere during assembly of the taper-locking mechanism, so that the channel into which the wedge and rod are positioned is always visible and accessible.

Figure 7:
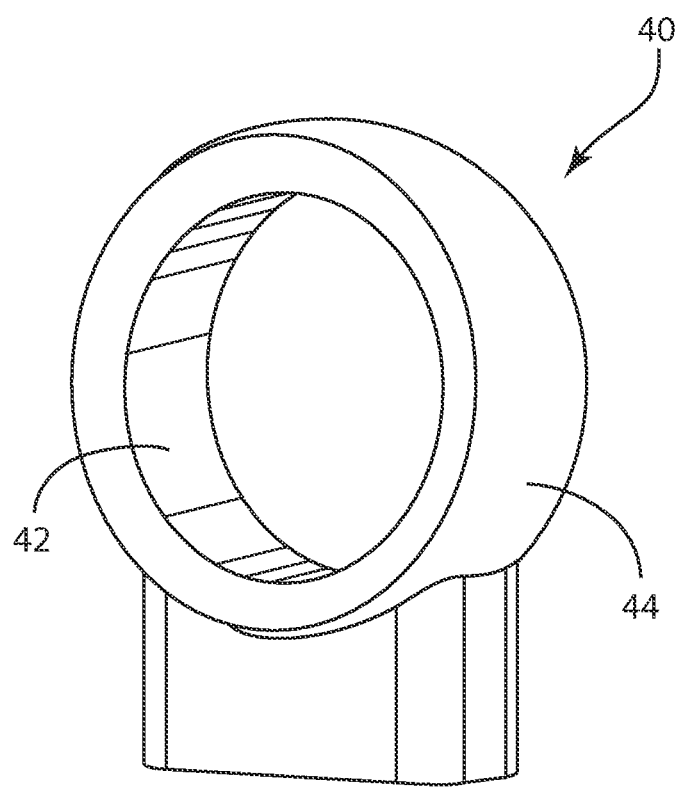
FIG. 7 is a perspective view of an implant member which may use a taper lock system for rod fixation.

The implant portion of the spinal rod fixation system consists of implant member 40 containing a concave spherical inner surface 42, as shown in FIG. 7. The radius of inner surface 42 is equal to the outer radius of spherical collet 30, so that implant member 40 provides a housing which can easily receive collet 30. Inner surface 42 may be roughened to help generate the frictional forces necessary for the polyaxial lock-out. Outer surface 44 of the implant member is shown as circular in FIG. 7, but may conceivably consist of any other geometry. The portion of implant 40 shaped to receive the collet 30, wedge 20, and rod 10 may also be referred to as a housing. Elements of the implant member 40 beyond its use in rod fixation may be used for spinal fixation, facet arthroplasty, or other applications. Implant member 40 may also be mounted to screws, hooks, artificial joints, crossbar and cross members, or other applications.

Figure 8:
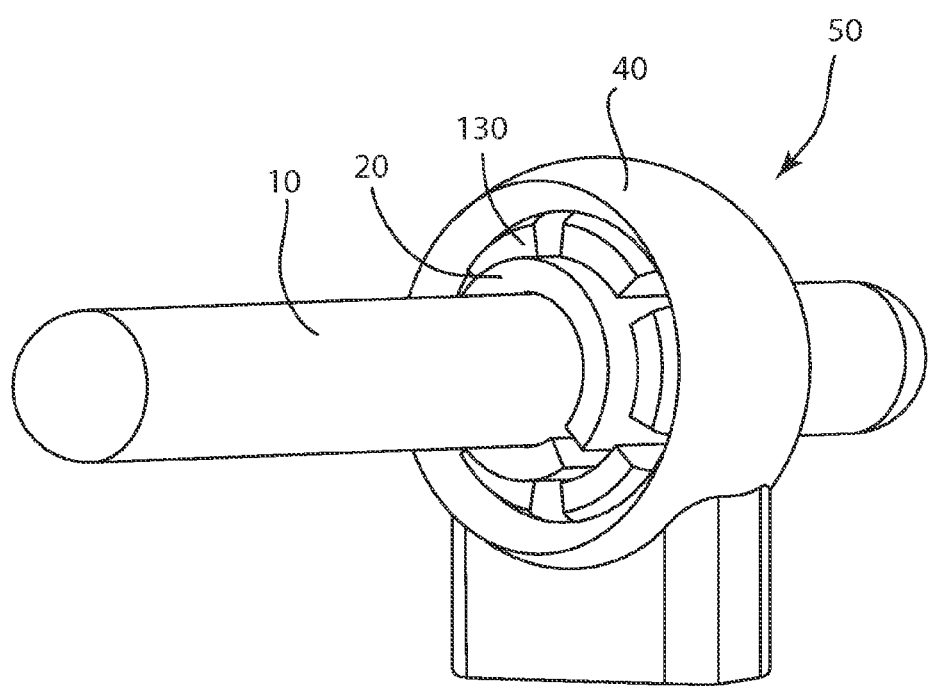
FIG. 8 is a perspective view showing a rod fixation system consisting of the implant member of FIG. 7, the spherical collet of FIG. 5, the tapered wedge of FIG. 3, and the cylindrical rod of FIG. 2.
Figure 9:
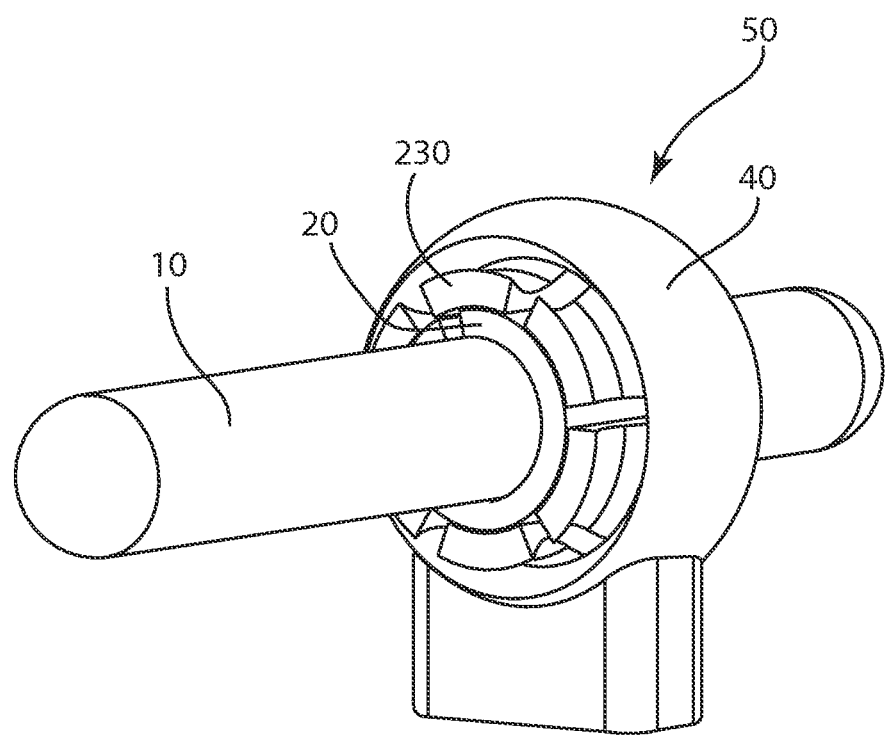
FIG. 9 is a perspective view showing a rod fixation system consisting of the implant member of FIG. 7, the spherical collet of FIG. 6, the tapered wedge of FIG. 3, and the cylindrical rod of FIG. 2.
Figure 10:
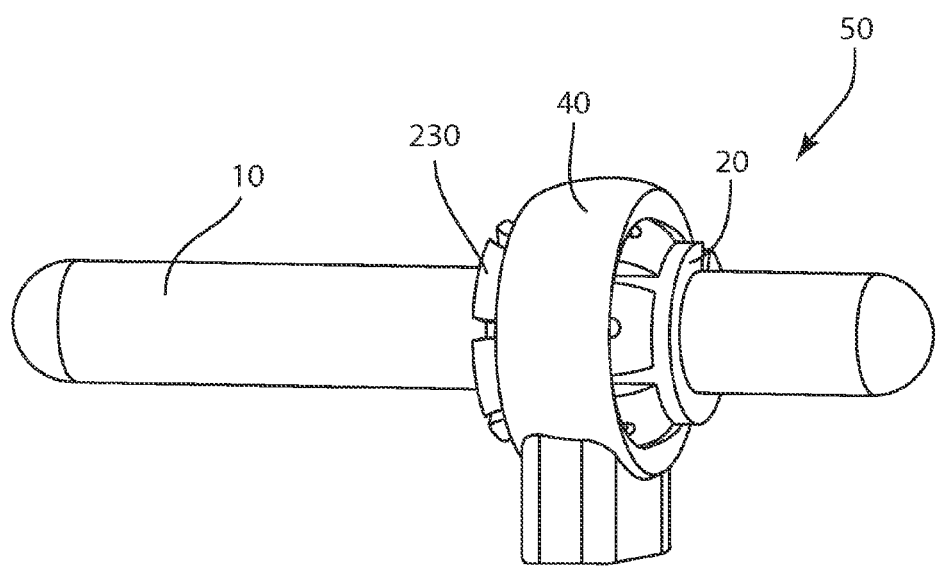
FIG. 10 is perspective view showing the side of the rod fixation system of FIG. 9.

The assembly 50 of the taper lock mechanism herein described is depicted in FIGS. 8, 9 and 10. Cylindrical rod 10 passes through tapered wedge 20. Wedge portion 20 articulates concentrically within a spherical collet, which is positioned within the spherical inner radius housing of implant member 40. FIG. 8 shows assembly 50 which uses spherical collet 130, while FIGS. 9 and 10 depict assembly 50 with flanged spherical collet 230.

Figure 11:
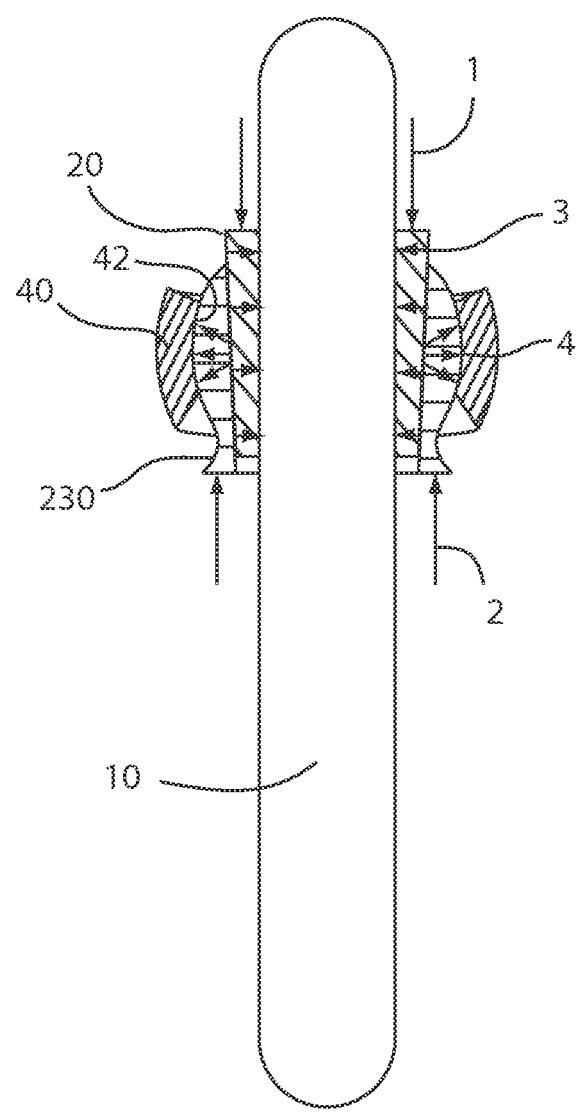
FIG. 11 is a cross-sectional view of the rod fixation system of FIG. 9 in lock-out.

Lock-out occurs by pressing tapered wedge 20 into the spherical collet along the longitudinal axis of rod 10, as shown in FIG. 11. Forces 1 and 2 are applied on wedge 20 and the opposite side of flanged spherical collet 230 to achieve insertion of tapered wedge 20. Forces 1 and 2 may be applied manually, or a separate tool (not shown) may be used to apply the forces. As tapered wedge 20 is pressed into spherical collet 230, the contact forces between wedge 20 and spherical collet 230 cause tapered wedge 20 to compress around cylindrical rod 10. This compression force, shown by arrows 3, locks rod 10 in position along its length. The insertion of wedge 20 into collet 30 also simultaneously expands spherical collet 230, causing its outer surface to press against inner surface 42 of implant 40. This expansion, denoted by arrows 4, locks spherical collet 230 and thereby wedge 20 and rod 10 within the implant 40, eliminating polyaxial motion and maintaining the desired orientation of rod 10 relative to the implant 40. Lock-out of a taper lock rod fixation system using a non-flanged spherical collet, such as the system depicted in FIG. 8 including collet 130, is accomplished in the same manner.

Figure 12:
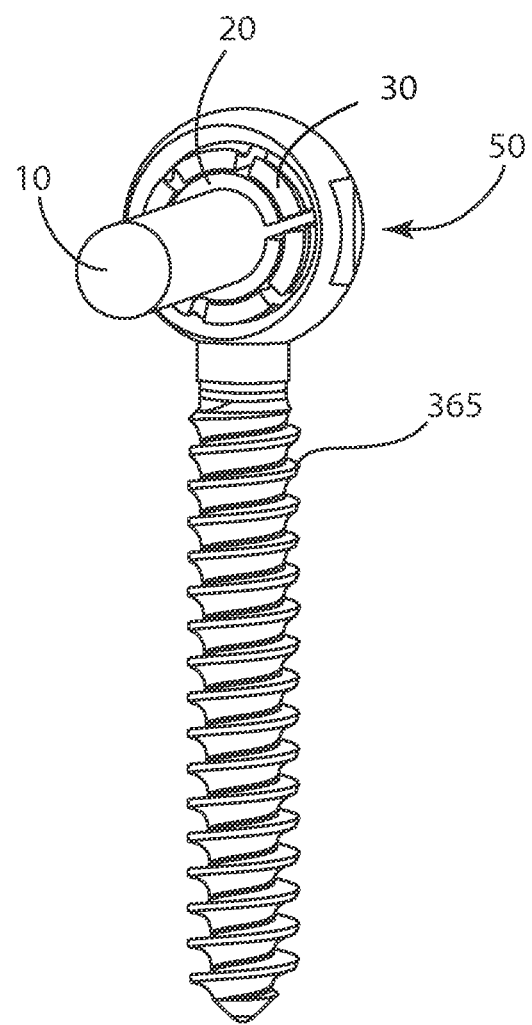
FIG. 12 is a perspective view of the taper lock feature used by a monolithic eyelet pedicle screw.

FIGS. 12-20 show multiple embodiments of the taper lock rod fixation system. All systems incorporate the core concept of the present invention, using a tapered interface to increase contact force around spherical collet 30 as a lock-out mechanism to secure rod 10 and collet 30 within the implant member. FIG. 12 is a perspective view of a monolithic member comprised of eyelet pedicle screw 365 and the taper lock feature 50 securing rod 10. Taper lock assembly 50 includes wedge 20 and spherical collet 30 contained within a housing 367 of eyelet pedicle screw 365.

Figure 13:
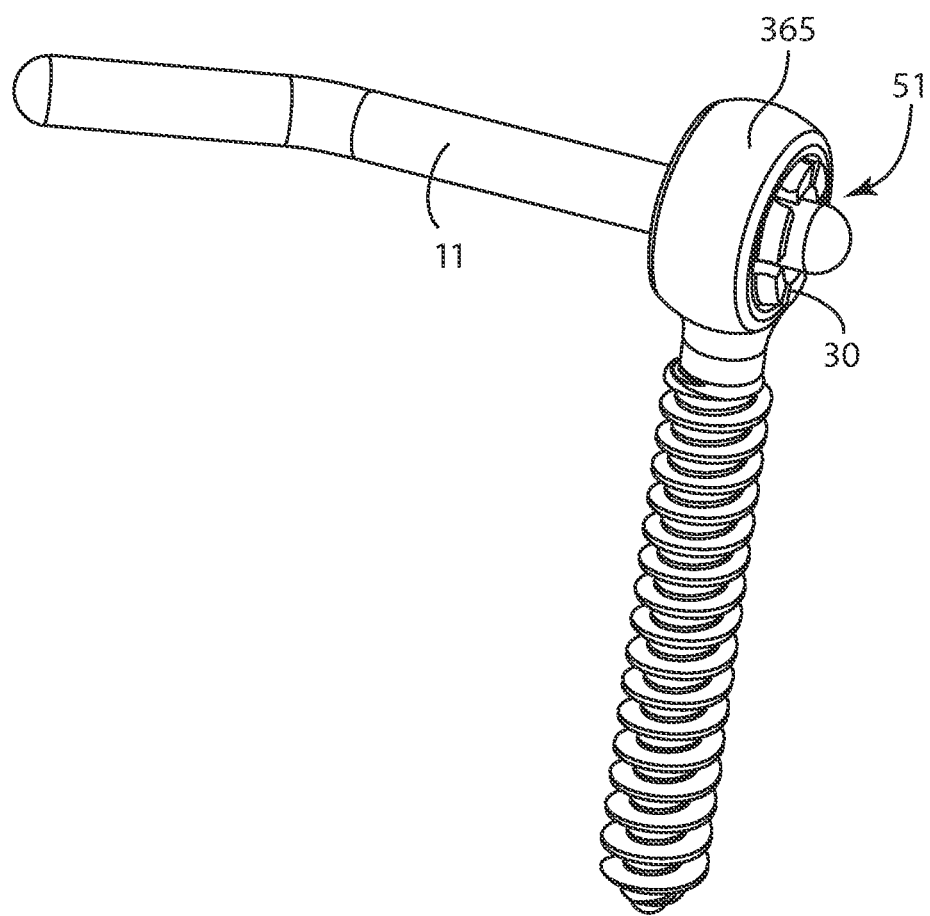
FIG. 13 is a perspective view of an alternative embodiment of the taper lock feature utilizing the monolithic pedicle screw of FIG. 12 and a taper integrally formed on the rod.
Figure 14:
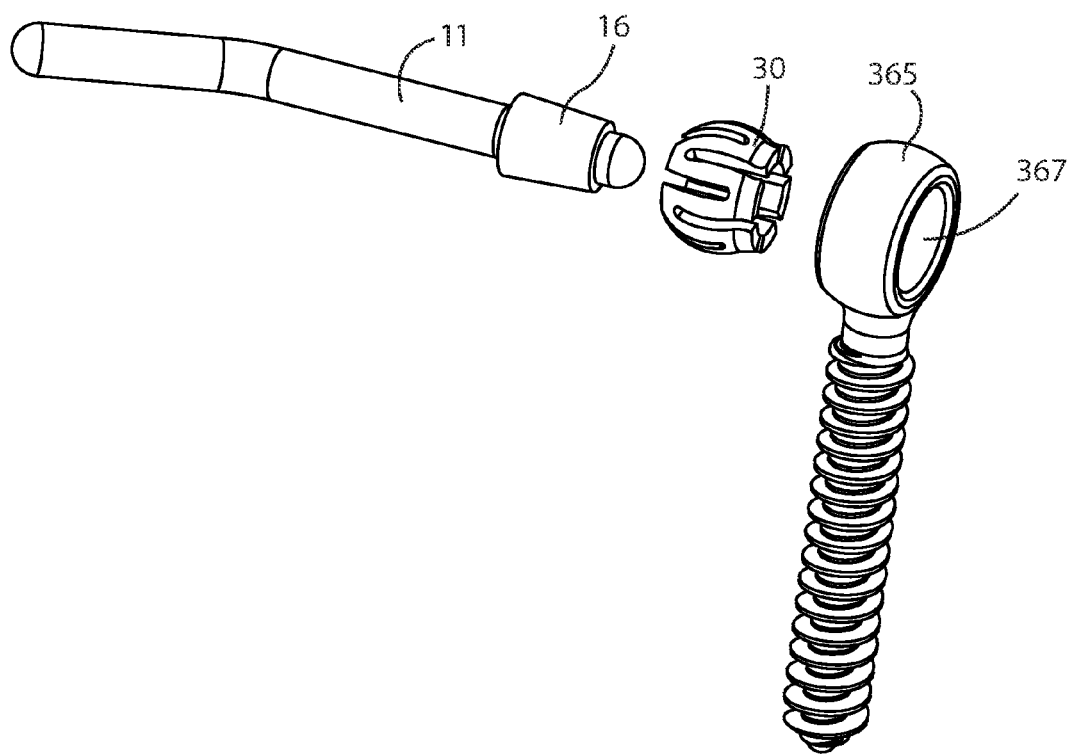
FIG. 14 is an exploded view of the assembly of FIG. 13.

FIGS. 13 and 14 show an alternative embodiment 51 of the taper lock feature. Taper lock 51 is shown to hold rod 11 within eyelet pedicle screw 365. Taper lock 51 does not include tapered wedge 20, however. Instead, rod 11 has a tapered section built into the rod. As seen in FIG. 14, the tapered section 16 is integrally formed as part of rod 11, which fits in spherical collet 30 and housing 367 of eyelet screw 365. Similar to the tapered wedge 20 of taper lock assembly 50, tapered section 16 may have a degree of taper substantially equal to the degree of taper of the channel of the collet. When rod 11 is pressed into collet 30 and the housing of the eyelet screw 365, the tapered section 16 engages with the channel of the collet 30, eventually causing the collet 30 to radially expand, and engage with the housing 367. The outer surface of the collet 30 and inner surface of the housing 367 may be roughened to provide increased friction.

Figure 15:
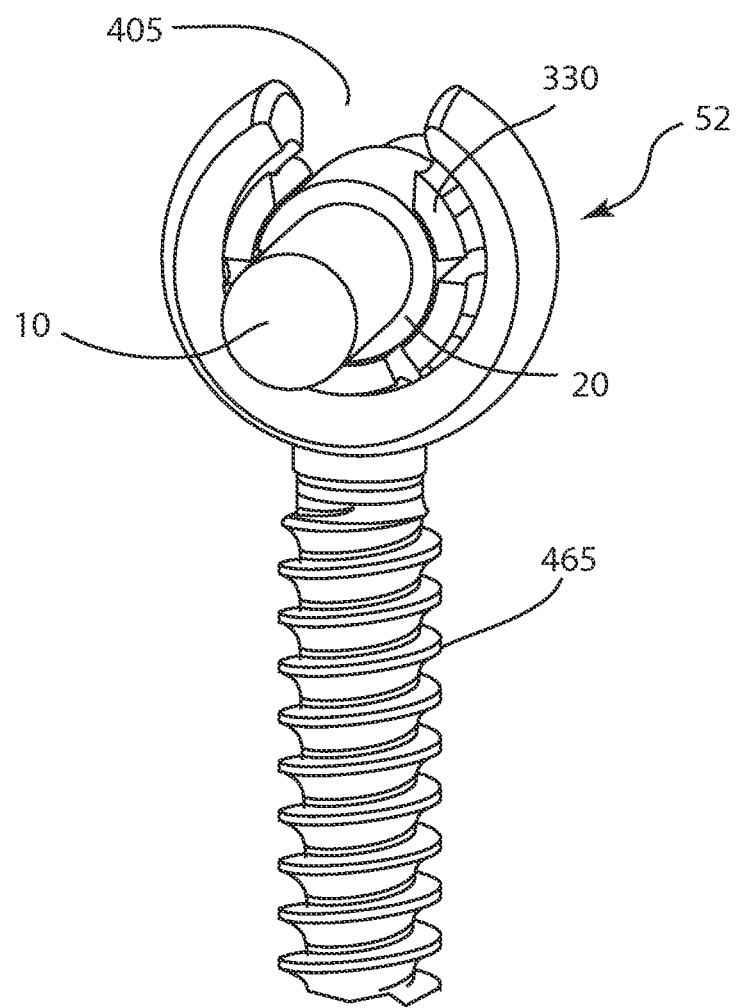
FIG. 15 is a perspective view of an alternative embodiment of the taper lock feature used by an open eyelet screw.

FIG. 15 is a perspective view of an implant member comprised of open eyelet screw 465 and an alternative embodiment 52 of the taper lock feature with opening 405 on the top surface of implant member 465 to facilitate top loading of rod 10 and tapered wedge 20. A split collet 330 enables drop-in placement of the rod and wedge.

Figure 16:
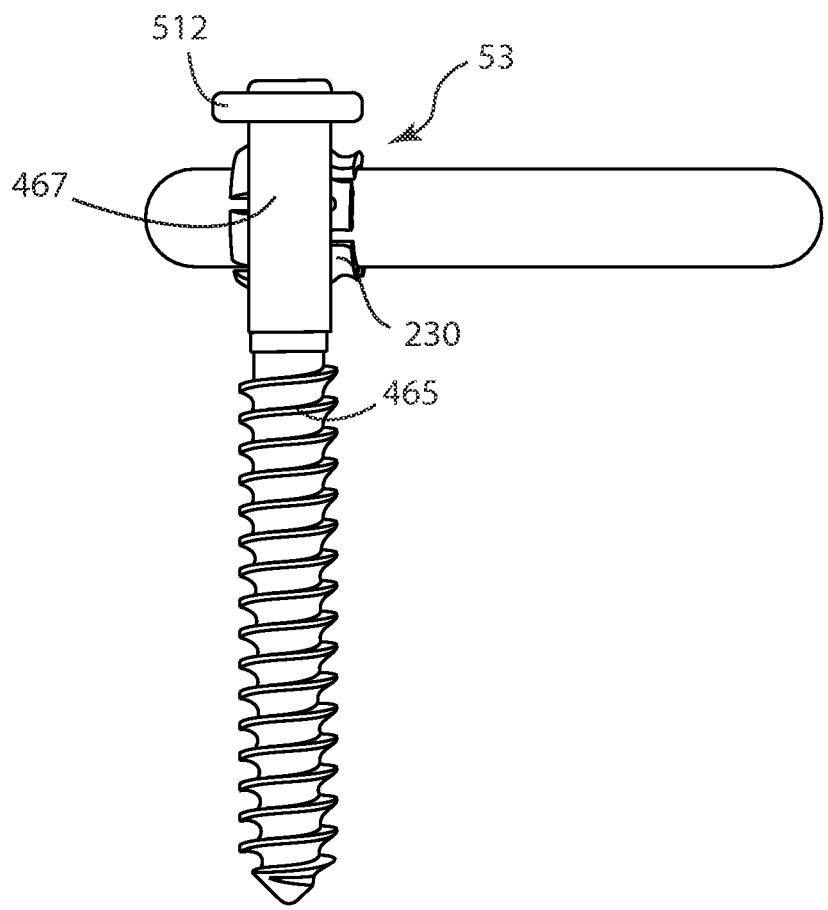
FIG. 16 is a lateral view of an alternative embodiment of the taper lock feature used by an open eyelet screw with a retainer.
Figure 17:
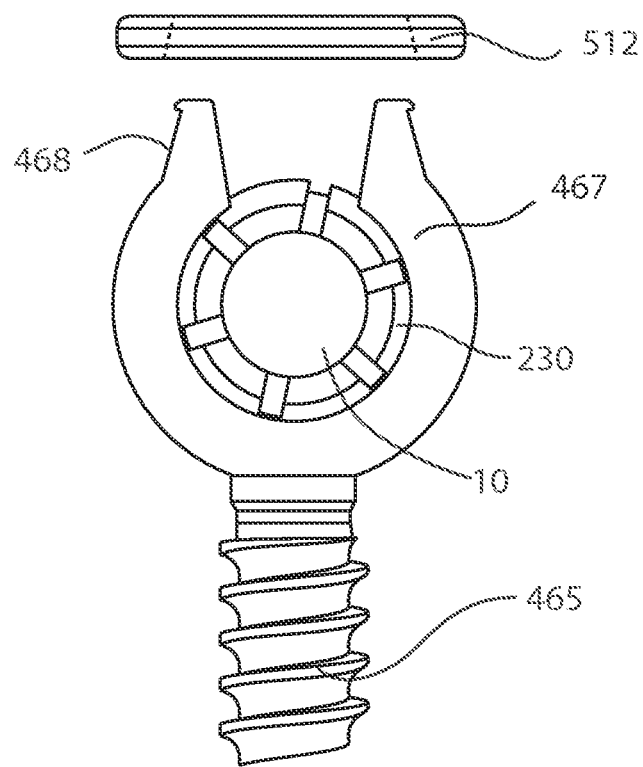
FIG. 17 is a wireframe view of the assembly of FIG. 16.

FIGS. 16 and 17 depict another open eyelet screw 465 with alternative taper lock 53, which does not require a tapered wedge 20. Instead, eyelet screw 465 includes retainer 512. As shown in FIG. 17, retainer 512 is tapered as well as top flanges 468 of eyelet screw 465. Spherical collet 230 is placed inside concave housing 467, and rod 10 is inserted into the collet 230. Retainer 512 is pushed down over flanges 468 of eyelet screw 465, squeezing them together to engage and compress spherical collet 230 and grip rod 10. After assembly, flanges 468 are retained in the compressed position by the retainer 512.

Figure 18:
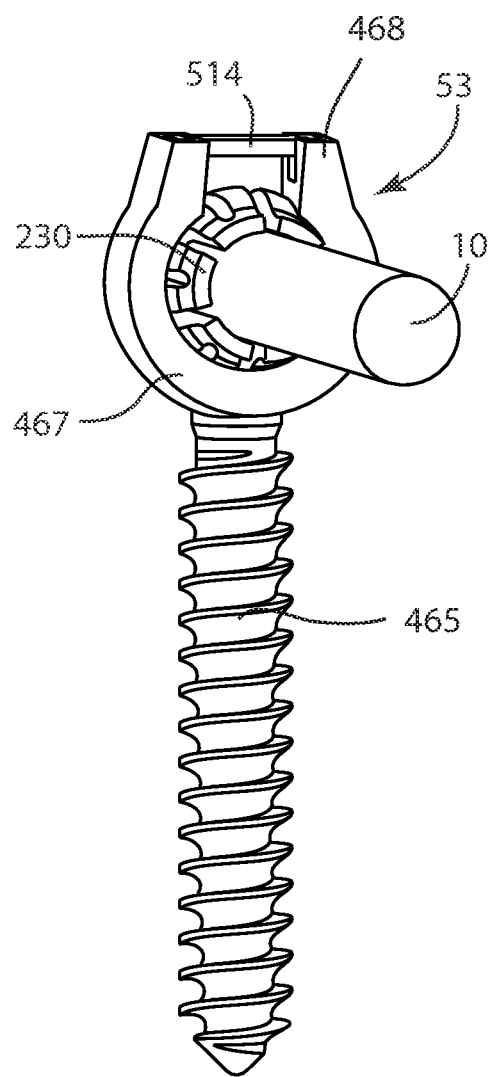
FIG. 18 is a perspective view of an alternative embodiment of the taper lock feature used by an open eyelet screw with a dogbone retainer.
Figure 19:
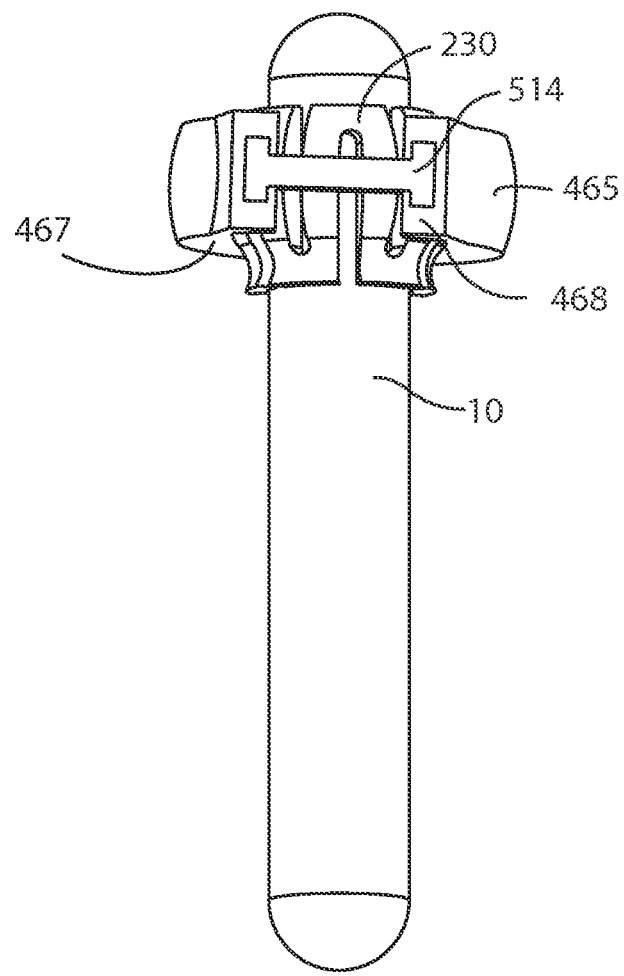
FIG. 19 is a top view of the assembly of FIG. 18.
Figure 20:
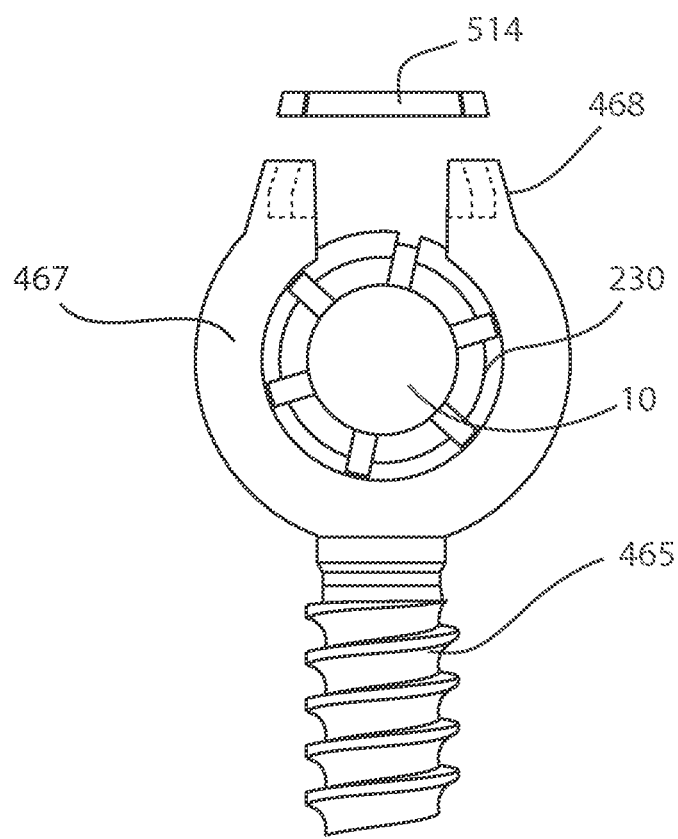
FIG. 20 is a wireframe view of the assembly of FIG. 18.

An alternative embodiment of taper lock 53 is shown in FIGS. 18-20. FIG. 18 shows taper lock 53 which is composed of rod 10, spherical collet 230, open eyelet screw 465, and dogbone retainer 514. As seen in FIGS. 19 and 20, dogbone retainer 514 and flanges 468 on eyelet screw 465 have tapered surfaces so that flanges 468 are pulled together as retainer 514 is inserted into flanges 468. Housing 467 is consequently closed around spherical collet 230, engaging and compressing spherical collet 30 and gripping rod 10.

Figure 21:
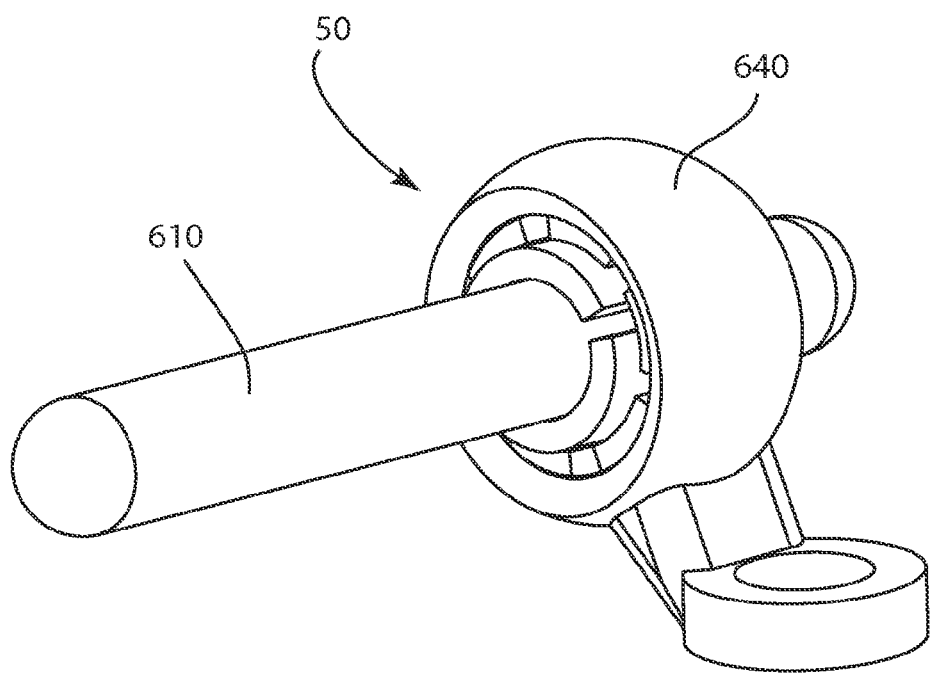
FIG. 21 is a perspective view of the taper lock feature applied to a stackable implant member.
Figure 22:
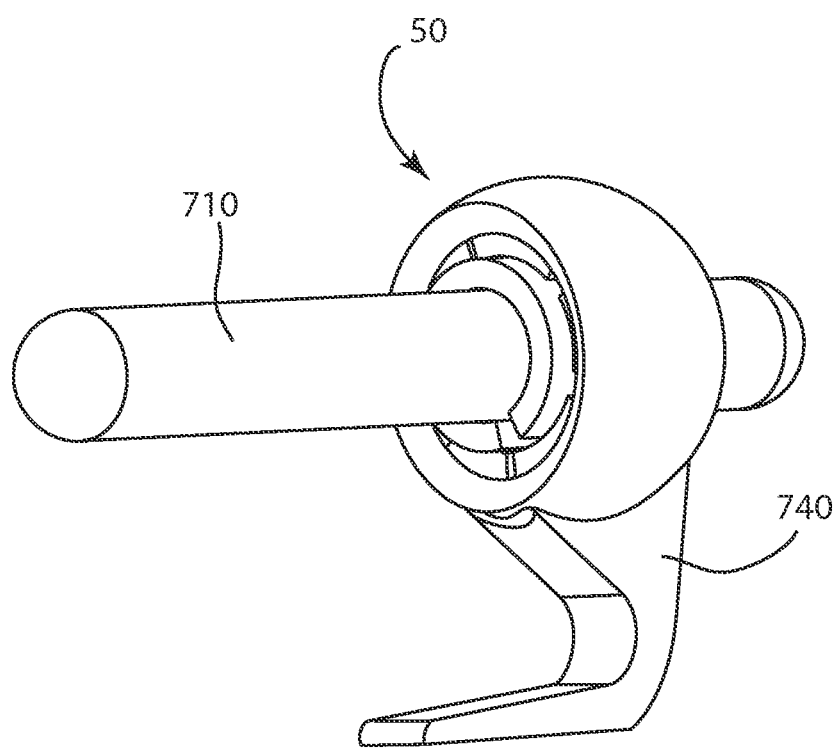
FIG. 22 is a perspective view of the taper lock feature applied to a spinal hook.

Applications of the present invention may include spinal fixation using screws or hooks or similar interfaces, as depicted in FIGS. 21-28. FIG. 21 is a perspective view of taper lock feature 50 applied to join rod 610 to stackable implant member 640, to be used in conjunction with a screw, post, or similar member. FIG. 22 is a perspective view of taper lock feature 50 applied to fix rod 710 in spinal hook 740.

Figure 23:
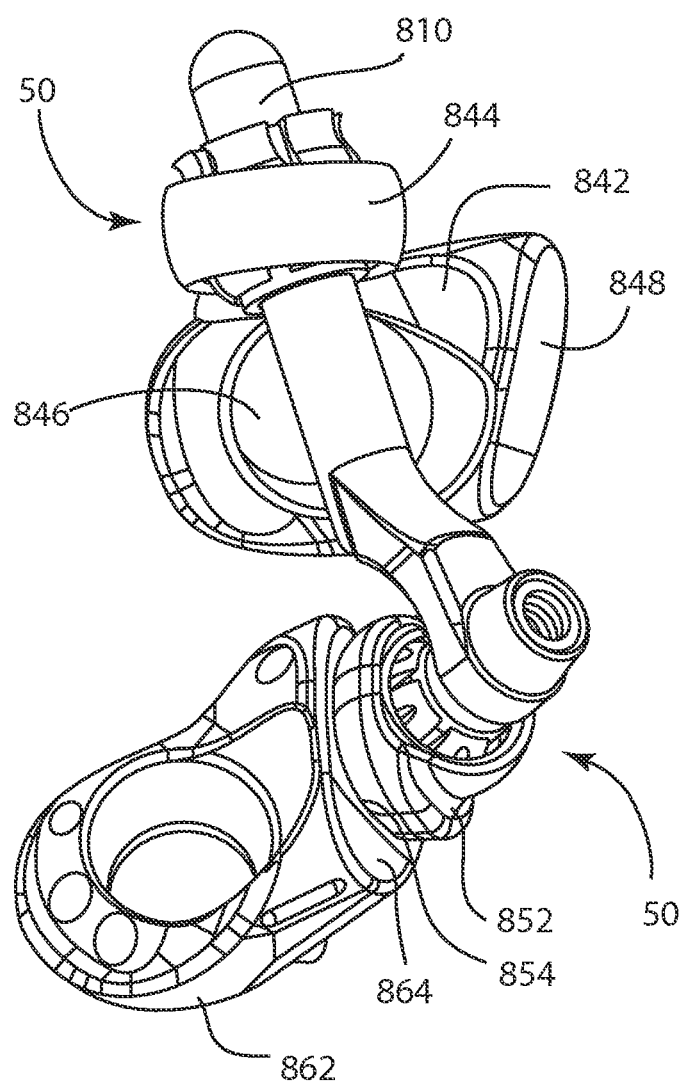
FIG. 23 is a perspective view of the taper lock feature applied to facet joint arthroplasty.

FIG. 23 is a perspective view of the taper lock system of the present invention applied to facet joint arthroplasty. Implantable superior facet member 842 comprises a housing 844, a fastener port 846 and a superior articulation surface 848. The housing 844 is shaped to secure a taper lock assembly 50. The fastener port 846 is shaped to receive a pedicle screw or other fastener or anchor, to secure the superior facet member 842 to a vertebra. The superior articulation surface 848 is shaped to articulate with an inferior facet member or natural inferior facet. A taper lock assembly 50 secures the cephalad end of cylindrical rod 810 to the superior member 842 within the housing 844.

Caudal to the superior facet member 842, an inferior facet member 852 is secured by a second taper lock assembly 50, or another polyaxial connection, to the caudal end of the rod 810. Inferior facet member 852 has an inferior articulation surface 854 which articulates with a second superior facet articulation surface 864 on a second superior facet member 862. Superior facet member 862 is similar to superior facet member 842 except that it does not have a housing for a taper lock connection. For multi-level facet arthroplasty, superior facet member 862 may be replaced with a superior facet member 842, which may connect, via a second taper lock connection, with a second rod and inferior facet member.

Figure 24:
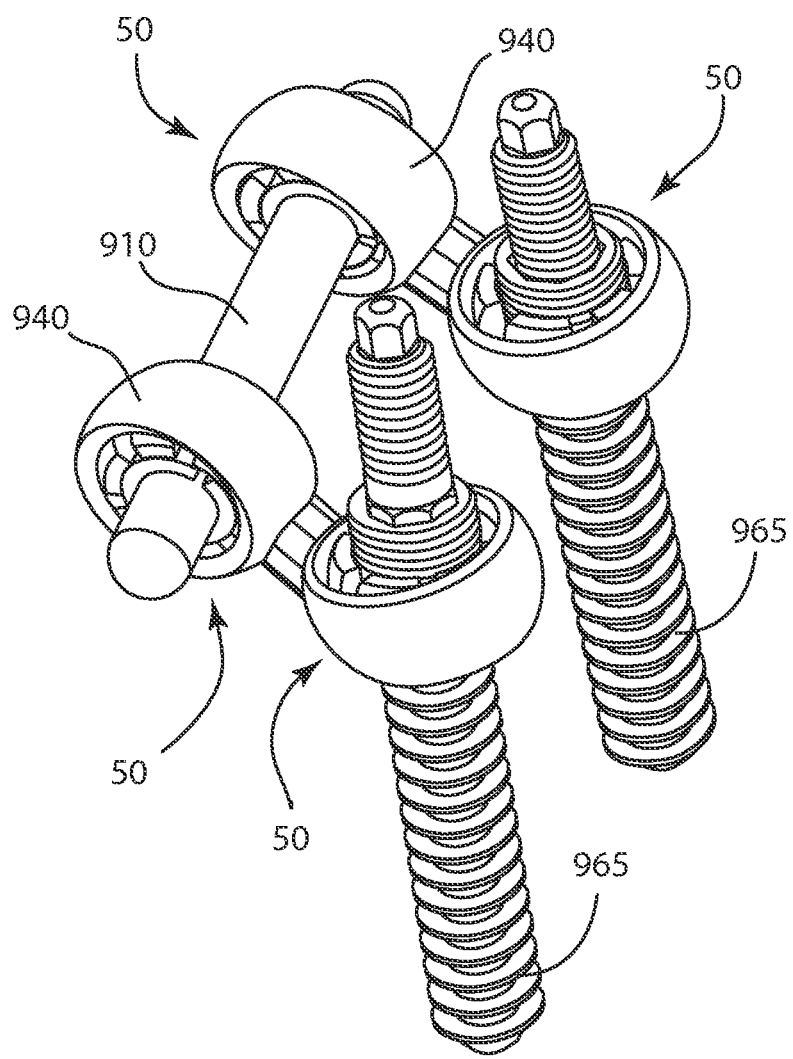
FIG. 24 is a perspective view of the taper lock feature used in a spinal rod fixation system.

FIG. 24 is a perspective view of a spinal rod fixation system which utilizes the taper lock system of the present invention to provide rigid support between two vertebrae. Fixation to the bone is achieved through pedicle screws 965 shown. Taper lock assembly 50 may be used to secure spinal rod 910 to spinal implant members 940. Taper lock assembly 50 may also be used to secure pedicle screws 965 within spinal implant members 940. Using taper lock assemblies allows individualized positioning and orientation of the rod 910 relative to the two pedicle screws 965. A longer rod may be used with additional pedicle screws 965 and taper lock assemblies 50 to provide rigid support across additional vertebral levels.

Figure 25:
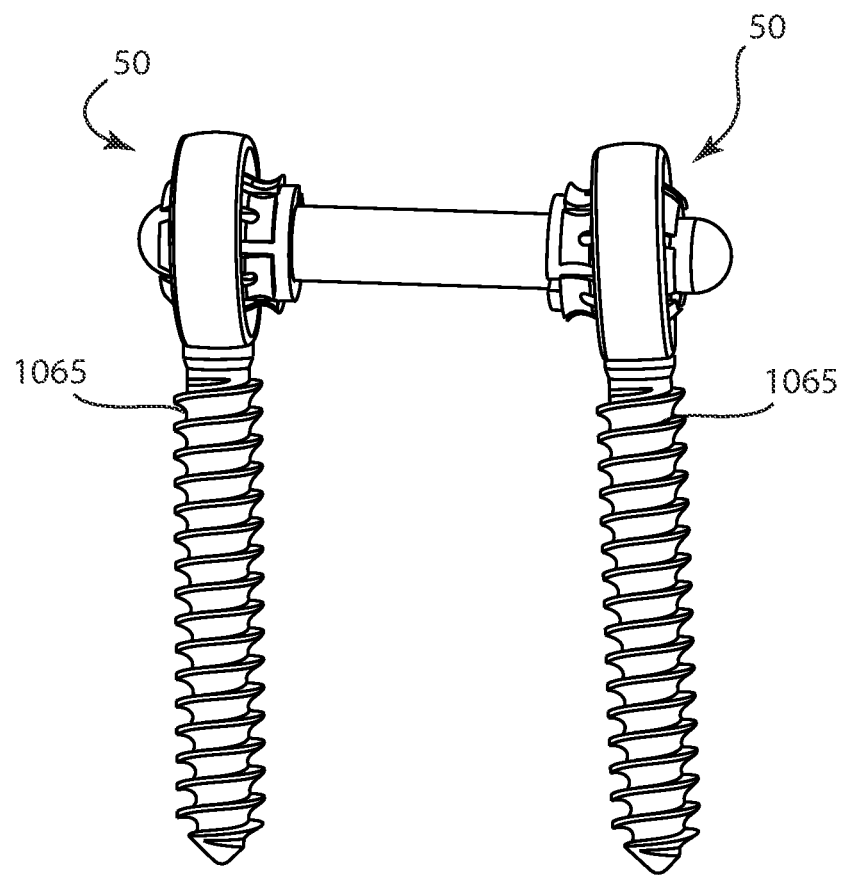
FIG. 25 is a side view of the taper lock feature used with eyelet screws as a pedicle fixation device.

FIG. 25 depicts a first eyelet screw 1065 with taper lock assembly 50 connected to a second eyelet screw 1065 with taper lock assembly 50 for pedicle-to-pedicle fixation.

Figure 26:
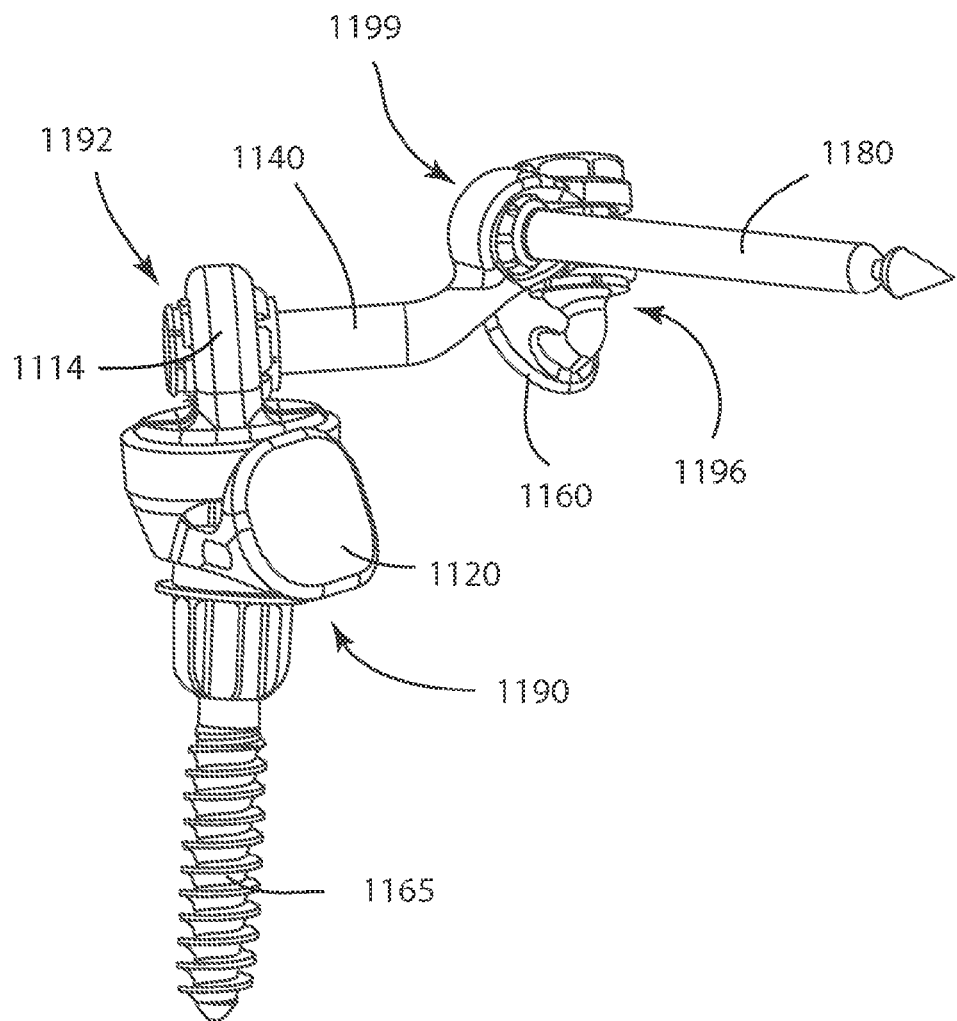
FIG. 26 is a perspective view of the taper lock feature used in a multi-level superior facet implant.
Figure 27:
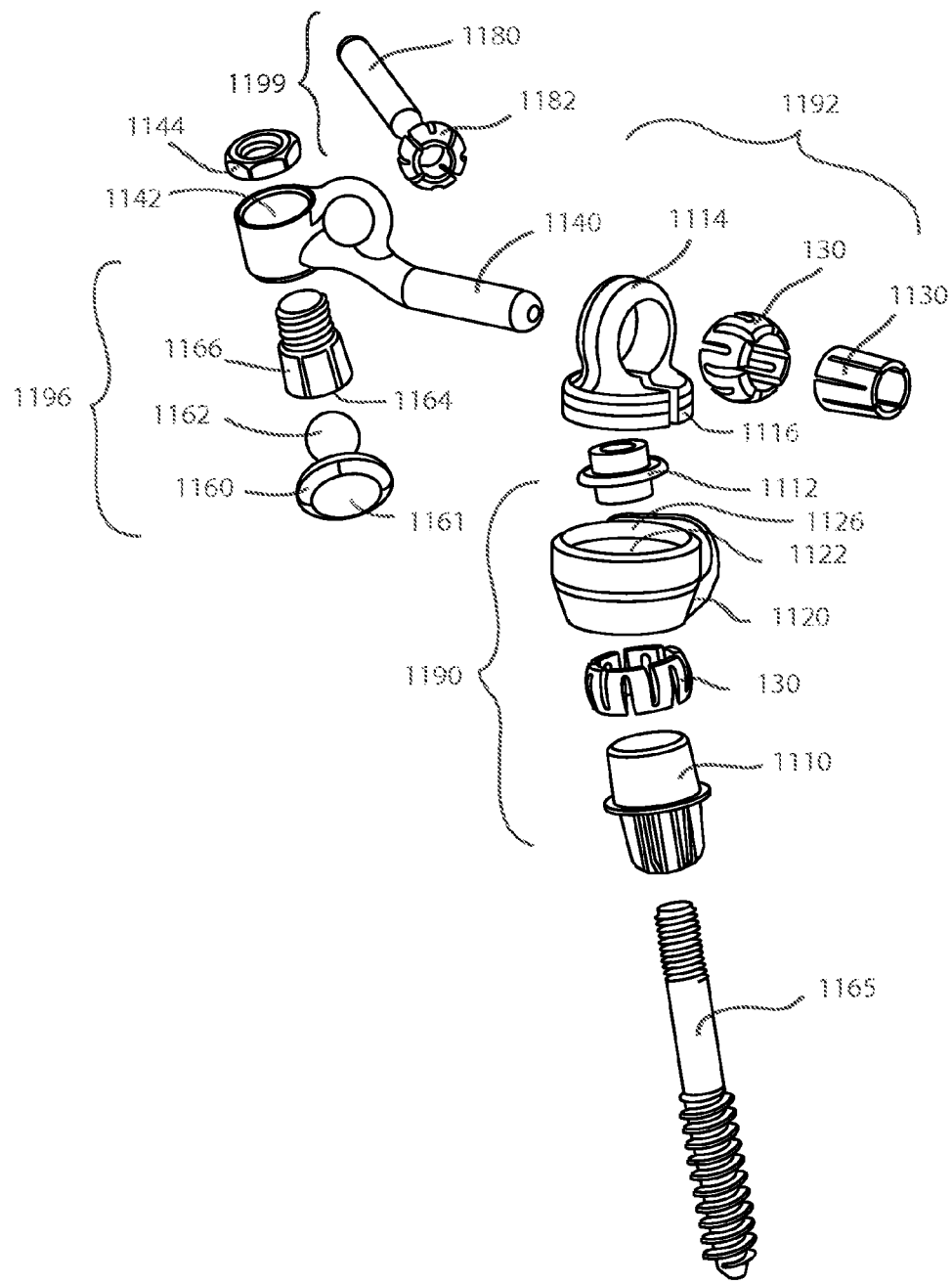
FIG. 27 is an exploded view of the assembly of FIG. 26.

FIGS. 26 and 27 show multiple embodiments of the taper lock used on a multilevel facet implant with a crossbar. FIG. 26 is a perspective view of the assembled implant, which includes a pedicle screw 1165, a superior member 1120, a linking rod 1140, an inferior member 1160 and a crossbar 1180. Three different taper locks are shown: taper lock 1190 locks superior member 1120 to the pedicle screw 1165, taper lock 1192 locks a split housing 1114 to the linking rod 1140, and taper lock 1196 locks the linking rod 1140 to the inferior member 1160. A polyaxial crosslink clamp 1199 links the linking rod 1140 to the crossbar 1180.

FIG. 27 is an exploded view of the assembly of FIG. 26. Taper lock 1190 comprises implantable pedicle screw 1165, wedge portion 1110, collet 130, and nut 1112. During assembly, wedge portion 1110 is slid onto implanted pedicle screw 1165. Spherical collet 130 is pre-assembled in an internal concave housing 1122 in the superior member 1120, and these are placed together over the wedge portion 1110. At this point, the superior member 1120 may be polyaxially rotated to attain its preferred orientation. Once the proper orientation is attained, a tool (not shown) is used to apply force to the collet 130 and the housing 1122, and the collet radially expands to engage the housing 1122 as it moves down the wedge portion 1110, and the orientation is locked. Simultaneously, the wedge portion may compress around the pedicle screw 1165, locking the wedge portion 1110 to the pedicle screw, or it may not compress around the screw and remain free to slide up and down the screw. Nut 1112 is placed in the collet 130 and screwed to the end of the pedicle screw 1165.

The linking rod 1140 is locked to the inferior member 1160 with a taper lock 1196. In taper lock 1196, the positions of the spherical member (the collet in other embodiments) and the wedge are reversed from their positions in other embodiments. The inferior member 1160 includes an inferior articulation surface 1161, and a sphere 1162, which is sized to fit into a spherical housing 1164 within a slotted tapered wedge 1166. During pre-assembly, the sphere 1162 is fitted into the spherical housing 1164 and together they are fitted into a ring 1142 on the inferior end of the linking rod 1140. The orientation of the inferior member 1160, and thus the inferior articulation surface 1161, may be set by rotating the sphere 1162. A nut 1144 is placed over the end of the slotted tapered wedge 1166, and as the nut is tightened, the slotted tapered wedge 1166 tightens around the sphere 1162, locking the orientation of the inferior member 1160. Crossbar 1180 and collet 1182 are locked to the linking rod 1140 with the polyaxial crosslink clamp 1199.

A split housing 1114 connects the linking rod 1140 with the pedicle screw assembly. Collet 130 is placed inside the split housing 114, and the housing is pinched and snapped into the top of the concave housing 1122 in the superior member 1120. When the split housing 1114 is pushed down sufficiently, a tapered rim 1116 on the flanges of the housing engages with a tapered rim 1126 on the housing 1122, and the split housing 1114 is snapped into place. Once snapped in and prior to lock-out, the split housing 1114 may be rotatable, thus allowing rotation of the position of the inferior member 1160 and the crossbar 1180.

Taper lock 1192 comprises the linking rod 1140, the split housing 1114, and collet 130, and a slotted tapered wedge 1130. The slotted tapered wedge 1130 is positioned within the channel of collet 130, and linking rod 1140 (with the inferior member 1160 and crossbar 1180 now attached) is inserted into the slotted tapered wedge 1130. Using a tool such as pliers or a similar tool, compression forces are applied to the opposite ends of the slotted wedge and the collet, in the same manner as illustrated in FIG. 11. The interaction between the tapered channel in the collet 130 and the slotted tapered wedge 1130 cause the wedge to compress around the linking rod 1140 while the collet 130 radially expands and engages the split housing 1114, thus locking the position and orientation of the linking rod 1140. The split housing 1114 is also locked in position relative to the housing 1122, because as the collet 130 expands and engages the split housing 1114, the split housing 1114 consequently expands and engages the housing 1122.

Figure 28:
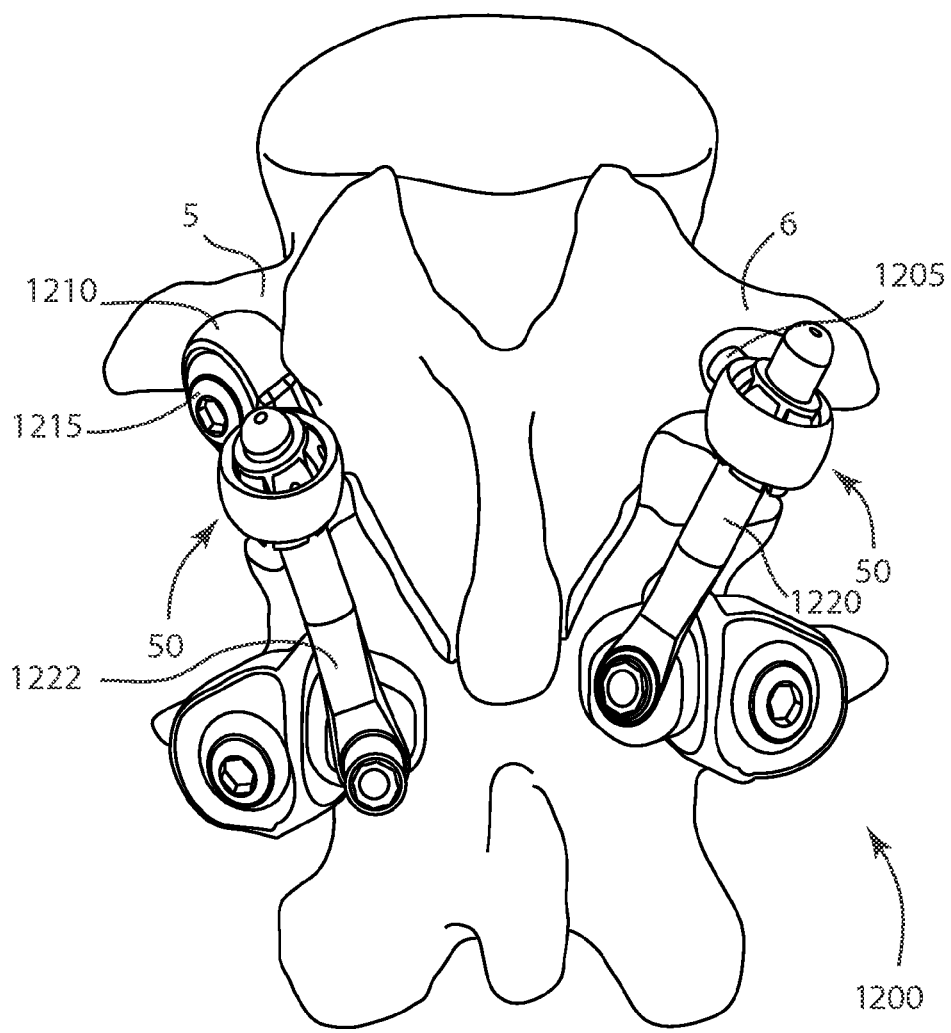
FIG. 28 is a posterior view of the taper lock feature used in a single level facet replacement.

FIG. 28 shows a bilateral single level facet replacement 1200 using taper lock technology to fasten the inferior facet members to the pedicles. Left and right sides show two different embodiments of taper lock assembly 50 and attachment to pedicles 5 and 6. On pedicle 6, a taper lock assembly 50 is used to lock an inferior facet member 1220 directly to an eyelet pedicle screw 1205 which is implanted in the pedicle. On pedicle 5, a taper lock assembly 50 locks an inferior facet member 1222 to a first end of a linking member 1210. A polyaxial connection which may be a taper lock affixes a second end of the linking member 1210 to a pedicle screw 1215.

The present invention includes variances of the system herein described. Alternative embodiments may include different geometries, intermediate parts, etc. Additional parts may include locking nuts or other fasteners to secure the position of the wedge, collet and rod. Changes in the geometry, especially on the ends of wedge 20 or collet 30, could be made to facilitate instrumentation or overall function. Applications of the present invention may include spinal fixation using screws or hooks or similar interfaces. The taper lock system may also be used by cross bars or cross linking systems to connect spinal implants and/or rods, as well as single- or multi-level facet joint replacement, or other iterations in which a rod or rod-like member is fixed to a second member.

The present invention may be embodied in other specific forms without departing from its spirit or essential characteristics. It is appreciated that various features of the above-described examples can be mixed and matched to form a variety of other alternatives. For example, wedge or collet configuration features can vary, as can the type of implant retaining the taper-lock fixation system. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:
1. A system, comprising:
 an implant shaped to replace a first portion of a first natural facet joint, the implant comprising a first facet articular surface;
 an elongated member; and a locking connector coupled to the implant, wherein the locking connector is configured to lock an orientation and/or a position of the implant relative to the elongated member, the locking connector comprising:
  a housing;
  a collet receivable within the housing, the collet comprising a channel; and
  a tapered wedge portion;
  wherein the collet is radially expandable, wherein the locking connector is configured to lock an orientation and/or position of the housing relative to the elongated member in response to radial expansion of the collet by non-rotatable insertion of the tapered wedge portion into the channel of the collet,
  wherein the tapered wedge portion includes a channel for receiving the elongated member, and
  wherein a first end of the elongated member is polyaxially movable relative to a second end of the elongated member prior to the locking connector locking an orientation and/or position of the housing relative to the elongated member.

2. The system of claim 1, further comprising a pedicle screw for selective attachment to a vertebra comprising the first portion of the first natural facet joint, wherein one of the elongated member and the housing is secured to the pedicle screw.

3. The system of claim 1, wherein the elongated member comprises a pedicle screw for selective attachment to a vertebra comprising the first portion of the first natural facet joint.

4. The system of claim 1, wherein the wedge portion comprising a bore shaped to receive the elongated member, wherein the wedge portion comprises an outer tapered wall configured to induce expansion of the collet in response to urging of the wedge portion into the channel.

5. The system of claim 4, wherein the channel comprises an inner tapered wall, and wherein the degree of taper of the outer tapered wall is substantially equal to the degree of taper of the inner tapered wall.

6. The system of claim 1, wherein the collet comprises a monolithic outer convex wall comprising a plurality of slots radially distributed about the outer convex wall to enable substantially uniform radial expansion of the collet.

7. The system of claim 1, wherein the housing and the first facet articular surface are formed as a single piece with each other.

8. The system of claim 1, wherein the housing comprises an inner concave wall and the collet comprises an outer convex wall, wherein at least one of the inner concave wall and the outer convex wall comprises a roughened surface.

9. The system of claim 1, further comprising: a second implant configured to replace a second portion of the first natural facet joint, the second implant comprising a second facet articular surface, wherein the second facet articular surface is configured to articulate with the first facet articular surface.

10. The system of claim 9, further comprising: a third implant configured to replace a first portion of a second natural facet joint; and a fourth implant configured to replace a second portion of the second natural facet joint; wherein the second natural facet joint is either one motion segment caudal or one motion segment cephalad to the first natural motion segment.

11. An implantable locking connector, comprising:
  an elongated member formed of a biocompatible material;
  a housing;
  a tapered wedge portion; and
  a collet shaped to be received by the housing, the collet comprising a monolithic outer convex wall comprising a plurality of slots radially distributed about the outer convex wall to enable substantially uniform radial expansion of the collet;
  wherein the collet is radially expandable,
  wherein the locking connector is configured to lock an orientation and/or position of the housing relative to the elongated member in response to radial expansion of the collet by non-rotatable insertion of the tapered wedge portion into the collet,
  wherein the tapered wedge portion includes a channel for receiving the elongated member, and
  wherein a first end of the elongated member is polyaxially movable relative to a second end of the elongated member prior to the locking connector locking an orientation and/or position of the housing relative to the elongated member.

12. The locking connector of claim 11, wherein the outer convex wall is substantially spherical, wherein the housing comprises an inner concave wall with a substantially spherical shape, wherein the collet further comprises a lip portion extending from the outer convex wall to limit relative rotation between the housing and the collet.

13. The locking connector of claim 11, wherein the housing comprises an inner concave wall, wherein at least one of the inner concave wall and the outer convex wall comprises a roughened surface.

14. The locking connector of claim 11, wedge portion is sized to receive the elongated member and be received in the collet, wherein the wedge portion comprises an outer tapered wall and the collet comprises an inner tapered wall, and wherein the degree of taper of the outer tapered wall is substantially equal to the degree of taper of the inner tapered wall.

15. A system, comprising:
  a first anchor attachable to a first bone;
  a second anchor attachable to a second bone;
  an elongated member rigidly attachable to the first anchor; and
  a locking connector configured to couple the elongated member to the second anchor, wherein the locking connector is configured to lock an orientation and/or a position of the second anchor relative to the elongated member, the locking connector comprising:
    a housing;
    a tapered wedge portion; and
    a collet receivable within the housing, the collet comprising a channel shaped to receive one of the tapered wedge portion and the second anchor;
    wherein the collet is radially expandable, wherein the locking connector is configured to lock an orientation and/or position of the housing relative to the received elongated member or second anchor in response to radial expansion of the collet by non-rotatable insertion of the tapered wedge portion into the collet to substantially prevent motion of the first bone relative to the second bone,
    wherein the tapered wedge portion includes a channel for receiving the elongated member, and
    wherein a first end of the elongated member is polyaxially movable relative to a second end of the elongated member prior to the locking connector locking an orientation and/or position of the housing relative to the elongated member.

16. The system of claim 15, wherein the collet comprises a channel shaped to receive the second anchor, wherein the locking connector is configured to lock an orientation and/or position of the housing relative to the second anchor in response to radial expansion of the collet to engage the housing to substantially prevent motion of the first bone relative to the second bone.

17. The system of claim 15, wherein the collet comprises a channel shaped to receive the elongated member, wherein the locking connector is configured to lock an orientation and/or position of the housing relative to the second anchor in response to radial expansion of the collet to engage the housing to substantially prevent motion of the first bone relative to the second bone.

18. The system of claim 15, wherein the first and second anchors comprise pedicle screws and the elongated member comprises a rod, such that the system comprises a pedicle screw and rod system configured to substantially prevent motion of the first bone relative to the second bone.

19. The system of claim 15, wherein the wedge portion comprises a bore shaped to receive one of the elongated member and the second anchor, wherein the wedge portion comprises an outer tapered wall configured to induce expansion of the collet in response to urging of the wedge portion into the channel.

20. The system of claim 19, wherein the channel comprises an inner tapered wall, and wherein the degree of taper of the outer tapered wall is substantially equal to the degree of taper of the inner tapered wall.

21. The system of claim 15, wherein the collet comprises a monolithic outer convex wall comprising a plurality of slots radially distributed about the outer convex wall to enable substantially uniform radial expansion of the collet.

22. The system of claim 15, wherein the housing comprises an inner concave wall and the collet comprises an outer convex wall, wherein at least one of the inner concave wall and the outer convex wall comprises a roughened surface.

* * * * *